(12) United States Patent
Murray et al.

(10) Patent No.: US 7,993,690 B2
(45) Date of Patent: Aug. 9, 2011

(54) CARBOHYDRATE AND ELECTROLYTE REPLACEMENT COMPOSITION

(75) Inventors: Robert Murray, Fox River Grove, IL (US); Craig A. Horswill, Barrington, IL (US); Robert F. Ferraro, Arlington Heights, IL (US); Dennis H. Passe, Hebron, IL (US); John R. Stofan, IV, Lake Zurich, IL (US); Chan T. Du, Schaumburg, IL (US)

(73) Assignee: Stokely-Van Camp, Inc., Chicago, IL (US)

( * ) Notice: Subject to any disclaimer, the term of this patent is extended or adjusted under 35 U.S.C. 154(b) by 89 days.

(21) Appl. No.: 12/273,609

(22) Filed: Nov. 19, 2008

(65) Prior Publication Data

US 2009/0148566 A1   Jun. 11, 2009

Related U.S. Application Data

(63) Continuation of application No. 10/706,420, filed on Nov. 12, 2003, now abandoned.

(51) Int. Cl.
*A23L 1/304* (2006.01)
*A23L 2/38* (2006.01)

(52) U.S. Cl. .......... 426/74; 426/567; 426/590; 426/648; 426/658

(58) Field of Classification Search .................. 426/590, 426/567, 74, 648, 658
See application file for complete search history.

(56) References Cited

U.S. PATENT DOCUMENTS

| | | | |
|---|---|---|---|
| 3,894,148 A | 7/1975 | Ecker | |
| 4,237,118 A | 12/1980 | Howard | |
| 4,309,417 A | 1/1982 | Staples | |
| 4,312,856 A | 1/1982 | Korduner et al. | |
| 4,322,407 A | 3/1982 | Ko | |
| 4,448,770 A | 5/1984 | Epting, Jr. | |
| 4,582,705 A | 4/1986 | Primes et al. | |
| 4,592,909 A | 6/1986 | Winer et al. | |
| 4,649,051 A | 3/1987 | Gyllang et al. | |
| 4,689,228 A | 8/1987 | Rosenberg | |
| 4,738,856 A | 4/1988 | Clark | |
| 4,853,237 A | 8/1989 | Prinkkila et al. | |
| 4,871,550 A * | 10/1989 | Millman | 424/601 |
| 4,871,554 A | 10/1989 | Kalala et al. | |
| 4,874,606 A | 10/1989 | Boyle et al. | |
| 4,938,970 A | 7/1990 | Hustead et al. | |
| 4,975,286 A | 12/1990 | Hechter | |
| 4,981,687 A | 1/1991 | Fregly et al. | |

(Continued)

FOREIGN PATENT DOCUMENTS

CA   896486   3/1972

(Continued)

OTHER PUBLICATIONS

Nose, et al., "Role of osmolality and plasma volume during rehydration in humans", American Physiological Society, 1988.

(Continued)

*Primary Examiner* — Helen F Heggestad
(74) *Attorney, Agent, or Firm* — Banner & Witcoff, Ltd.

(57) ABSTRACT

The present invention discloses novel compositions and methods. These compositions and methods may be used to attenuate or reverse the effects of dehydration or other adverse effects of exercise, heat or other activity which causes bodily fluid loss. The novel compositions comprise carbohydrates, electrolytes and water along with flavoring agents.

16 Claims, 35 Drawing Sheets

U.S. PATENT DOCUMENTS

| | | | |
|---|---|---|---|
| 5,011,826 A | 4/1991 | Steudle et al. | |
| 5,028,437 A | 7/1991 | Jerrett | |
| 5,032,411 A | 7/1991 | Stray-Gundersen | |
| 5,089,477 A | 2/1992 | Fregley et al. | |
| 5,112,622 A | 5/1992 | Kopp | |
| 5,114,723 A * | 5/1992 | Stray-Gundersen | 426/74 |
| 5,200,200 A | 4/1993 | Veech | |
| 5,248,507 A | 9/1993 | e Silva et al. | |
| 5,397,786 A | 3/1995 | Simone | |
| 5,443,830 A | 8/1995 | Moore et al. | |
| 5,443,848 A | 8/1995 | Kramer et al. | |
| 5,447,730 A | 9/1995 | Greenleaf | |
| 5,455,235 A | 10/1995 | Takaichi et al. | |
| 5,464,619 A | 11/1995 | Kuznicki et al. | |
| 5,498,426 A | 3/1996 | Wilson et al. | |
| 5,498,427 A | 3/1996 | Menasche | |
| 5,597,595 A | 1/1997 | DeWille et al. | |
| 5,609,897 A | 3/1997 | Chandler et al. | |
| 5,681,569 A | 10/1997 | Kuznicki et al. | |
| 5,780,094 A | 7/1998 | King | |
| 5,817,351 A | 10/1998 | DeWille et al. | |
| 5,824,353 A | 10/1998 | Tsunoda et al. | |
| 5,830,523 A | 11/1998 | Takaichi et al. | |
| 5,846,572 A | 12/1998 | Prior | |
| 5,869,458 A | 2/1999 | Waite et al. | |
| 5,968,544 A * | 10/1999 | Howard et al. | 424/439 |
| 6,020,007 A | 2/2000 | Veech | |
| 6,056,989 A | 5/2000 | Sasagawa et al. | |
| 6,103,274 A | 8/2000 | Jettka et al. | |
| 6,106,874 A | 8/2000 | Liebrecht et al. | |
| 6,207,203 B1 | 3/2001 | Atkinson et al. | |
| 6,235,322 B1 | 5/2001 | Lederman | |
| 6,251,457 B1 | 6/2001 | Takaichi et al. | |
| 6,261,610 B1 | 7/2001 | Sher et al. | |
| 6,319,490 B1 | 11/2001 | Parker | |
| 6,451,352 B1 | 9/2002 | Yvin et al. | |
| 6,478,985 B2 | 11/2002 | Idaka | |
| 6,485,764 B2 | 11/2002 | Robergs et al. | |
| 6,572,898 B2 | 6/2003 | Nelson et al. | |
| 6,730,337 B2 | 5/2004 | Hutt et al. | |
| 7,001,612 B2 | 2/2006 | Armonti et al. | |
| 2001/0043908 A1 | 11/2001 | Parker | |
| 2001/0051197 A1 | 12/2001 | Yang et al. | |
| 2002/0009502 A1 | 1/2002 | Nelson et al. | |
| 2002/0044992 A1 | 4/2002 | Parker | |
| 2002/0099023 A1 | 7/2002 | Boucher, Jr. | |
| 2002/0102313 A1 | 8/2002 | Armonti et al. | |
| 2002/0110621 A1 | 8/2002 | Robergs et al. | |
| 2002/0119183 A1 | 8/2002 | Hermelin et al. | |
| 2002/0132034 A1 | 9/2002 | Hutt et al. | |
| 2002/0132214 A1 | 9/2002 | Mattson et al. | |
| 2002/0176885 A1 | 11/2002 | Najafi et al. | |
| 2003/0021875 A1 | 1/2003 | Blank et al. | |
| 2003/0077333 A1 | 4/2003 | Phillips et al. | |
| 2003/0119755 A1 | 6/2003 | Mazer | |
| 2003/0134804 A1 | 7/2003 | King et al. | |
| 2003/0194448 A1 | 10/2003 | Mitchell et al. | |
| 2003/0203072 A1 | 10/2003 | O'Mahony et al. | |
| 2005/0095271 A1 | 5/2005 | Mathewson | |

FOREIGN PATENT DOCUMENTS

| | | |
|---|---|---|
| EP | 0 364 053 | 4/1990 |
| EP | 0 587 972 A1 | 3/1994 |
| FR | 2770778 A1 * | 5/1999 |
| GB | 1 252 781 | 11/1971 |
| GB | 1252781 | 11/1997 |
| JP | 6332766 | 6/1980 |
| JP | 6016221 | 9/1981 |
| JP | 59098670 | 6/1984 |
| JP | 59210872 | 11/1984 |
| JP | 59220177 | 12/1984 |
| JP | 6112887 | 6/1986 |
| JP | 1060360 | 3/1989 |
| JP | 02083327 | 3/1990 |
| JP | 02211854 | 8/1990 |
| JP | 037251160 | 11/1991 |
| JP | 05219921 | 8/1993 |
| JP | 05276904 | 10/1993 |
| JP | 06038707 | 2/1994 |
| JP | 07067575 | 3/1995 |
| JP | 8501449 | 2/1996 |
| JP | 09155367 | 6/1997 |
| JP | 9508804 | 9/1997 |
| JP | 10501407 | 2/1998 |
| JP | 10502802 | 3/1998 |
| JP | 10150960 | 6/1998 |
| JP | 11089547 | 4/1999 |
| JP | 2000060506 | 2/2000 |
| JP | 2000125827 | 5/2000 |
| JP | 201190256 | 7/2001 |
| JP | 2001190255 | 7/2001 |
| JP | 2001259659 | 9/2001 |
| JP | 2001514022 | 9/2001 |
| JP | 2001299295 | 10/2001 |
| JP | 2001346556 | 12/2001 |
| JP | 2002017315 | 1/2002 |
| JP | 2002034501 | 2/2002 |
| JP | 2002 125639 | 5/2002 |
| JP | 2002125639 | 5/2002 |
| JP | 2002523025 | 7/2002 |
| JP | 2001333750 | 12/2004 |
| WO | WO 94/06412 | 3/1994 |
| WO | WO 95/22911 | 8/1995 |
| WO | WO9606539 | 3/1996 |
| WO | WO98/46091 | 10/1998 |
| WO | WO 99/11149 | 3/1999 |
| WO | WO 00/10402 | 3/2000 |

OTHER PUBLICATIONS

Figaro, et al., "Regulation of fluid intake in dehydrated humans: role of oropharyngeal stimulation", The American Physiological Society, 1997.

Gonzalez-Alonso, et al., Rehydration after Exercise with Common Beverage and Water, Int. J. Sports Med; 13; pp. 399-604; 1992.

Passe, et al., "Impact of beverage acceptability on fluid intake during exercise", Academic Press, 2000.

Clapp, et al., Effects of Carbohydrate-Electrolyte Content of Beverages on Voluntary Hydration in a Simulated Industrial Environment, AIHAJ; 61; Sep./Oct. 2000.

Nielsen, et al., "Fluid balance in exercise dehydration and rehydration with different glucose-electrolyte drinks", Eur J Appl Physiol; 55:318-325; 1986.

Wemple, et al. "Influence of Sodium Replacement on Fluid Ingestion Following Exercise-Induced Dehydration", International Journal Report Nutrition, 7, pp. 104-116, 1997.

The Effectiveness of Commercially Available Sports Drinks, Centre for Human Movement, University of Tasmania, Australia; Sports Medicine, Mar. 29, 2000.

* cited by examiner

CARBOHYDRATE AND ELECTROLYTE REPLACEMENT COMPOSITION

CROSS REFERENCE TO RELATED APPLICATIONS

This application is a continuation of pending U.S. Ser. No. 10/706,420, filed Nov. 12, 2003. The entire contents of this application are incorporated herein by reference.

FIELD OF INVENTION

The present invention relates to an improved rehydration beverage which provides for fluid, carbohydrate, and electrolyte replacement. The beverage comprised of a novel mineral blend enhances rehydration by providing superior voluntary fluid consumption and fluid retention. Non-fluid components of the beverage composition can be provided in forms other than beverages.

BACKGROUND OF THE INVENTION

There are currently available a number of beverages, and concentrated beverage compositions (including liquid, powdered or tablet concentrates) to be prepared by the consumer into a drinkable form, which are used for rehydration of fluids lost during exercise or vigorous activity. These rehydration beverages (also known as "sports drinks"), both in the ready-to-drink form and as prepared by the user, may be consumed before, during and after exercise. While these sports drinks rehydrate the body better than plain water, there remains a need for a superior rehydration beverage that addresses many aspects of rehydration such as voluntary fluid consumption and fluid retention.

Rehydration can be accomplished in a number of different ways. In the most basic sense, water replaces some of the fluids lost through sweat and helps maintain body temperature and important cardiovascular functions. Sports drinks have been developed which replace the fluids and electrolytes lost through sweat. This is an improvement over plain water not only because these drinks replace some of the minerals lost in sweat but also because carbohydrates are provided as a source of added energy. However, rehydration would be improved if the beverage also improved fluid retention, reduced urinary fluid loss, stimulated increased voluntary consumption, possessed superior sensory qualities, and supported the physiological response to continue drinking.

Conventional sports drinks typically contain water, small amounts of minerals/electrolytes and an energy source in the form of carbohydrate compounds. The scientific rationale for inclusion of common electrolytes such as sodium and potassium rested on the intuitive notion that it would be logical to replace some of the electrolytes lost in sweat. Stimulating voluntary fluid intake and promoting fluid retention were either secondary considerations or worse, not considered at all.

In addition, the mineral content of sports drinks varies widely. For instance some beverages can contain 5 mEq/L of sodium while others can contain over four times that amount. Similarly, there are wide differences in the content and amounts of other minerals, such as potassium, magnesium and chloride.

Some research has indicated that sodium content in fluid replacement beverages has a marked effect on fluid retention after exercise. Basically this research shows that when subjects ingest standard volumes of solutions containing sodium in the range of 40-100 milliequivalents per liter (mEq/L), rehydration is improved by increasing fluid retention and maintaining positive fluid balance. However, the palatability of a fluid replacement beverage containing an increased amount of sodium was not considered. Nadel E., Mack G., and Takamata, A., *Thermoregulation, Exercise, and Thirst: Interrelationships in Humans*. In *Perspectives in Exercise Science and Sports Medicine: Exercise, Heat, and Thermoregulation*, vol. 6, pp. 225-251, (Gisolfi, Lamb and Nadel eds., Indianapolis Ind., Brown and Benchmark, 1993); Maughan, R. J. and J. B. Leiper, *Sodium Intake and Post-Exercise Rehydration in Man*, Eur. J. Appl. Physiol. 71:311-319, (1995); Shirreffs, S. M. and R. J. Maughan, *Volume Repletion after Exercise Induced Volume Depletion in Humans: Replacement of Water and Sodium Losses*, Am. J. Physiol. 43:F868-F875, (1998). These articles are hereby incorporated by reference.

Fluid replacement after significant dehydration is driven by various physiological changes. The two major physiological drivers that encourage voluntary drinking are plasma osmolality and plasma volume. During exercise, the loss of fluid through sweat causes plasma volume to drop and plasma osmolality to increase. These physiological changes cause a thirst response which drives voluntary fluid consumption. Scientific studies have shown that sodium also plays an important role in regulating plasma volume and osmolality. Ingesting beverages containing sodium helps increase the rate at which plasma volume and osmolality return to normal. However, ingesting too high a level of sodium causes rapid restoration of plasma volume, which reduces the drinking response and prevents adequate rehydration. In addition, the sensory properties of a beverage containing too high a level of sodium are unfavorable, and would further reduce the drive to drink. Wemple, Richard D., Morocco, Tamara S., Mack, Gary W., *Influence of Sodium Replacement on Fluid Ingestion Following Exercised-Induced Dehydration*, Int'l J. Sport Nutrition & Exerc. Metabolism 7:104-116 (1997). This article is hereby incorporated by reference.

It is further believed that other electrolytes and minerals play an important role in rehydration by possibly affecting fluid replacement and fluid retention. In response to fluid loss during dehydration, water is distributed between fluid compartments so that both the extracellular and intracellular compartments share the water deficit. Sodium, potassium, magnesium, calcium and chloride are some of the more important electrolytes/minerals involved in filling these body fluid compartments, particularly sodium, chloride, potassium and magnesium. Beverages providing sodium and chloride encourage the filling of the extracellular compartment, while beverages providing potassium, magnesium, and calcium favor the filling of the intracellular compartment. Properly balancing the sodium, potassium, magnesium, calcium and chloride levels will further improve the rehydration properties of the beverage.

These electrolyte ions assist in filling these body fluid compartments more rapidly and help to retain the fluid instead of it being excreted as urine. Since both sodium and chloride ions favor the filling of the extracellular compartments, substitution of one with the other may not affect the overall result. The same may be true for potassium and magnesium in regards to intracellular hydration.

U.S. Pat. No. 4,981,687, issued to Fregly et al., incorporated herein, discloses a beverage comprising water, sugar, and electrolytes, an improvement wherein said beverage further comprises glycerol, pyruvate and/or caffeine. The sugar contained in the beverage claimed in this patent can be glucose, sucrose or other appropriate sugar compound, with glucose at a concentration of from about 2% to about 8% being specifically disclosed and glucose at a concentration of about 4% being preferred. Examples of electrolytes disclosed in this patent include 15-30 mEq/L sodium, 1-5 mEq/L potassium, 2-8 mEq/L phosphate, bicarbonate, sulfate, chloride, calcium, and magnesium.

The beverages as disclosed above are said to ameliorate the adverse physiological effects which can result from physical exertion and heat exposure. The present invention also seeks to address the adverse physiological effects of physical exertion, but without including stimulants or other chemical compounds which may have known acute effects (e.g. glycerol and pyruvate promoting gastrointestinal distress) and unknown long-term effects.

Therefore, a need exists for a rehydration beverage that supplies necessary electrolytes and energy sources, exhibits organoleptic properties which are substantially equivalent or superior to those of typical sports drinks, and provides superior rehydration by addressing several mechanisms affecting rehydration, such as fluid retention and voluntary fluid consumption. Furthermore, a need exists for a method that ameliorates the effects of dehydration, enhances rehydration, and addresses mechanisms such as fluid retention, and urinary loss.

The present invention fulfills these needs. The beverages of the present invention enhance rehydration, supply necessary electrolytes and energy sources, exhibit organoleptic properties at least substantially equivalent to other sports drinks, improve fluid retention and voluntary fluid consumption. The method of the present invention also addresses the above concerns through the administration of the composition of the present invention. The composition may be administered orally. And the composition can take many forms including but not limited to, liquid, gel, dry powder, tablet or capsule. Concentrated forms of the composition such as a powder can be can be added to water and/or other liquids which can include electrolytes and/or carbohydrates, including even sports drinks such as Gatorade® in order to provide beverages of the present invention.

Dehydration is reduced and fluid retention is improved by abating urinary loss when one embodiment of the present invention is taken during exercise, as illustrated in Example 2 hereof. Examples 3 through 7, further show that the present invention reduces the effects of dehydration, improves fluid retention, reduces urinary fluid loss, and possess superior sensory properties which should improve voluntary fluid consumption when taken after activity-induced fluid loss. It is further believed that similar results should be obtained when the beverage of the present invention is taken before activity-induced fluid loss.

SUMMARY OF THE INVENTION

The present invention relates to a beverage composition for oral consumption comprising: from about 4% to about 10% by weight of carbohydrates; at least about 30 mEq/L of beverage of sodium; at least about 7 mEq/L of beverage of potassium; from about 10 to about 20 mEq/L of beverage of chloride; from about 0% to about 0.4% of a flavoring agent, when present; from about 0 to about 100 parts per million (ppm) of a clouding agent, when present; from about 0.24% to about 0.38% by weight citric acid, when present; and typically balance water. Furthermore, the extracellular-favoring ions (especially sodium and chloride) may be present in combination at levels of from about 40 to about 78 mEq/L of beverage. These quantities are based on the total content of a finally prepared, complete beverage. It will be appreciated that the complete beverage can be fully formulated as noted above, or it can be made up by providing portions or all of a component or components by added liquids, whether the liquid is water or water already containing components adequate to prepare the final beverage. In the latter case, the formulation added to the liquid has components so as to make up the finally prepared beverage when the formulation and the liquid are combined to form the complete beverage.

The osmolality of the beverage is in the range of from about 250 to about 350 mOsm/Kg. The beverage also may include from about 1 to about 6 mEq/L of calcium; and when present, from about 1 to about 6 mEq/L of magnesium.

The present invention also relates to a beverage concentrate which is formulated to provide the beverage already described herein upon preparation by the consumer. The concentrate can take many forms including, but not limited to, gel, dry powder, tablet, capsule and liquid concentrates. The concentrates may be added to water and/or other liquids including water and carbohydrates and/or electrolytes, such as Gatorade®. Administration can be oral, intravenously, or by other suitable means.

BRIEF DESCRIPTION OF THE DRAWINGS

The advantages of the invention can be better understood by referring to the following drawings.

DETAILED DESCRIPTION OF THE INVENTION

Figure 1:
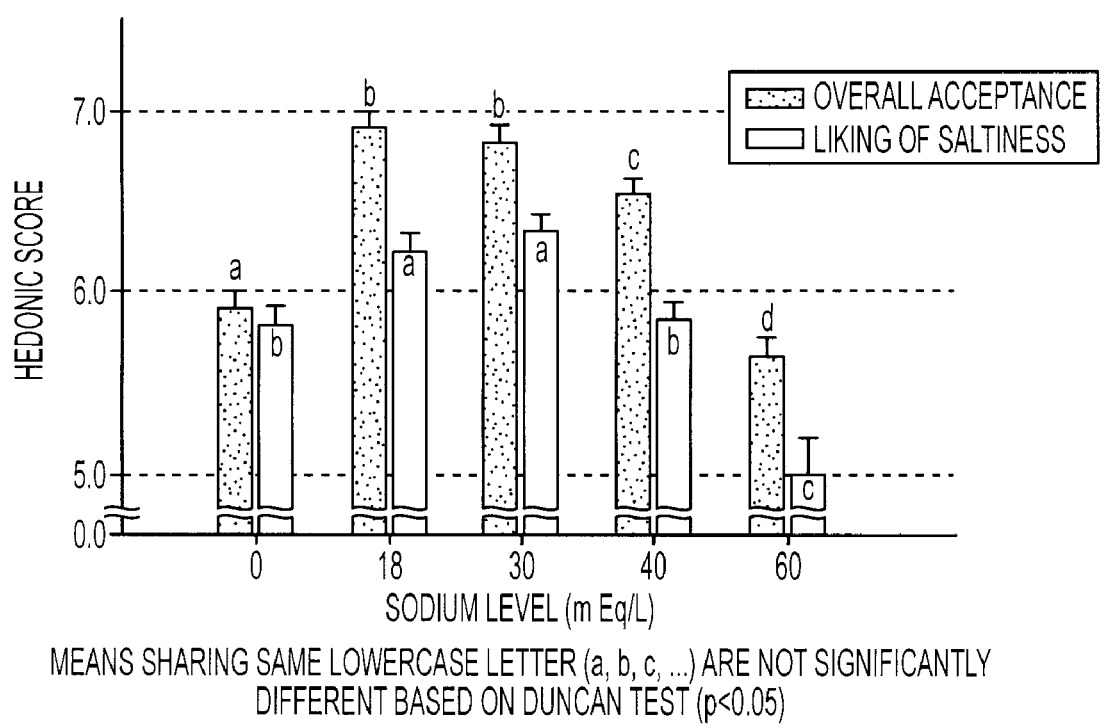
FIG. 1 shows the hedonic scores of various formulations with regard to overall acceptance and liking of saltiness when consumed during exercise.

The beverage of the present invention provides superior rehydration by improving fluid retention and reducing urine fluid loss. Additionally, the beverage enhances rehydration by also improving voluntary fluid intake. Moreover, the organoleptic or sensory properties of the beverage are at least as favorable as other sports drinks.

The beverage of the present invention optimizes the level of sodium and typically also chloride and potassium levels so as to maximize rehydration without compromising the sensory properties of the beverage. In addition, by including potassium, magnesium and chloride at especially advantageous levels, the rehydration effects are further improved without changing the palatability of the beverage. Furthermore, by maintaining the combination of extracellular-favoring ions at a level of between about 40-78 mEq/L, the advantageous rehydration and sensory properties are promoted.

The advantages discussed above have been demonstrated through a number of experiments. Various formulations were tested for various sensory properties. In addition, these formulations were tested for rehydration ability through the mechanisms of increased voluntary fluid consumption, increased fluid retention, and reduced urine loss. The first experiment to determine the taste characteristics of the beverage was performed on fifty athletes at rest. Of these experimental formulations, the preferred one had a sodium content of 30 mEq/L, had very good hedonic ratings, consistent with the leading sports drink in the U.S.

Improved voluntary fluid consumption of this formulation also has been shown. An experiment was conducted on 50 athletes that were allowed to drink ad libitum during an exercise protocol. This formulation was directionally favored over other sodium levels for this beverage in terms of voluntary fluid consumption. Another finding was that "salty" beverages become more palatable during and after exercise compared to at rest. In addition, dehydration was abated to a higher degree with this formulation.

Other testing was directed to fluid retention and urine-loss effects. Subjects were deprived of fluid during an exercise-induced dehydration period resulting in a loss of 2.5-3.0% of body weight. Following the exercise-induced dehydration, the subjects drank enough of the beverage formulations to equal the fluid lost through sweat. Results indicated significantly greater fluid retention with the experimental formulation having 30 mEq/L of sodium. Similarly, this formulation outperformed other experimental formulations in attenuating fluid loss in the form of urine. In addition, this formulation scored directionally higher hedonic ratings. While this formulation was liked equally well as another experimental formulation having 18 mEq/L of sodium, it was directionally favored over all other experimental formulations having different sodium levels for characteristics of sweetness, flavor, tartness, saltiness and overall acceptance.

Two more experiments were conducted in a similar fashion and with a similar purpose. The experimental formulation having 30 mEq/L of sodium remained the same. It was compared to different experimental formulations. In addition, blood and urine chemical analyses were conducted. The experimental formulation having 30 mEq/L of sodium had improved rehydration properties; urinary fluid loss was reduced, the percentage of fluid retained increased, and overall body weight change was greater.

Additionally, two experiments were conducted to determine the effects on rehydration, using similar methods, by combining sodium and chloride at certain concentration levels. The first of these experiments compared the 30 mEq/L of sodium formulation described above with experimental formulations containing 18 and 25 mEq/L of sodium. The 25 mEq/L formulation included an amount of chloride so that the combined level of these extracellular favoring ions was substantially higher than both the 30 or 18 mEq/L of sodium formulations. (See the formulation table in example 6). The 25 mEq/L formulation resulted in improved fluid retention compared to the other two formulations.

The second of these experiments compared the 30 mEq/L of sodium formulation with a 25 mEq/L of sodium formulation, but this time the combined levels of sodium and chloride were more closely matched in the two formulations. (See the formulation table in example 7). No differences in fluid retention were found between these formulations. However, the 25 mEq/L of sodium formulation received initial negative sensory ratings versus the formulation having 30 mEq/L of sodium, but less chloride.

The beverage of the present invention typically includes from about 4% to about 10%, preferably from about 5.5% to about 6.5%, more preferably about 6% by weight of a carbohydrate source. Carbohydrate sources, include but are not limited to, sucrose, maltose, maltodextrin, glucose, galactose, trehalose, fructose, fructo-oligosaccharides, beta-glucan, and trioses such as pyruvate and lactate. Preferably, a mixture of a minimum of three of these is formed, with the amount of fructose being less than the total amount of glucose from all carbohydrate sources. A preferred composition of carbohydrates comprises from about 1% to about 5% sucrose, from about 1% to about 2.5% glucose and from about 0.8% to about 1.8% fructose to produce a total of 6% carbohydrate, and more preferably from about 2 to about 4% sucrose, from about 1.4 to about 2% glucose, and about 1.1 to about 1.5% fructose, to produce a total of 6% carbohydrates.

The sodium content of the beverage of the present invention comprises at least about 30 mEq/L, preferably from about 30 to about 100 mEq/L of beverage, more preferably from about 30 to about 60 mEq/L of beverage, even more preferably from about 33 to about 40 mEq/L. This sodium concentration indicates the total amount of sodium present in the beverage, including sodium contained in the carbohydrate source, flavoring agent (to the extent known), and clouding agent. For example, maltodextrin as a carbohydrate source may contain sodium. However, these sources alone cannot raise the sodium levels of the beverage to the necessary levels, and as such additional sodium must be added from another sodium ion source.

Any source of sodium known to be useful to those skilled in the art can be used in the present invention. Examples of useful sodium sources include, but are not limited to, sodium chloride, sodium citrate, sodium bicarbonate, sodium lactate, sodium pyruvate, sodium acetate and mixtures thereof. A mixture of sodium chloride and sodium citrate being preferred, and a mixture of from about 10 to about 50 mEq/L, preferably from about 10 to about 30 mEq/L, and more preferably from about 10 to about 20 mEq/L of sodium from sodium chloride and from about 10 to about 50 mEq/L, preferably from about 10 to about 30 mEq/L, and more preferably from about 10 to about 20 mEq/L of sodium from sodium citrate.

In addition, the beverage of the present invention also includes chloride. The chloride ion can come from various sources known to those skilled in the art. Examples of chloride sources include, but are not limited to, sodium chloride, potassium chloride, magnesium chloride and mixtures thereof. The concentration of chloride is at least about 10 mEq/L, preferably from about 10 to about 20 mEq/L, more preferably from about 11 to about 18 mEq/L of chloride from sodium chloride.

Furthermore, the beverage of the present invention also preferably includes a combination of extracellular favoring ions, where the sum of these ions is from about 40 to about 78 mEq/L. This range can even be from about 42 to about 70 mEq/L or from about 46 to about 60 mEq/L. Sodium and chloride ions are some of the ions which favor the filling of the extracellular fluid compartment.

The beverage of the present invention also includes potassium. The potassium ion source can come from many sources known to those skilled in the art as being useful in the present invention. Examples of potassium sources useful herein include, but are not limited to, potassium monophosphate, potassium diphosphate, potassium chloride, and mixtures thereof, with potassium monophosphate being preferred. The potassium content is at least 8 mEq/L, preferably from about 8 to about 20, and more preferably at from about 10 to about 19 mEq/L.

The beverage of the present invention further preferably includes magnesium. The magnesium ion can also come from many sources known to those skilled in the art. Examples of magnesium sources include, but are not limited to, magnesium oxide, magnesium acetate, magnesium chloride, magnesium carbonate, magnesium diphosphate, magnesium triphosphate, magnesium in the form of an amino acid and mixtures thereof, with magnesium oxide being preferred. The concentration of magnesium is at a level of at least 0.1 mEq/L, preferably from about 0.5 to about 6 mEq/L, more preferably from 1 to 3 mEq/L.

Additionally, calcium preferably is present in the beverage of the present invention. The calcium ion may come from a variety of sources known to those skilled in the art. Examples include but are not limited to, calcium lactate, calcium carbonate, calcium chloride, calcium phosphate salts, calcium citrate and mixtures thereof, with calcium lactate being preferred. Calcium is present at a concentration of at least 0.1 mEq/L, preferably from about 0.5 to about 6 mEq/L, more preferably from 1 to 3 mEq/L.

A flavoring agent may be used in the beverage of the present invention. The flavoring agent of the beverage of the present invention also impacts the overall acceptance of the beverage. In order to achieve this overall acceptance, the strength of the flavor cannot be too intense. Of course, the flavor intensity of the beverage will depend upon the amount and type of the particular flavoring agent used. Furthermore, the same flavor from different suppliers may have differing intensity. Thus, it is difficult to quantify the level of flavoring agent necessary for the present invention. However, in general it has been found that a flavoring agent at a concentration of from about 0% to about 0.400% by weight is useful in the present invention. Furthermore, flavoring agents themselves may contain gum arabic, ester gum, starches such as, dextrins, "modified food starch", propylene glycol or alcohol. These additional components may acts as carriers or stabilizers.

In addition, any flavoring agent which satisfies the above criteria and is known to be useful to those skilled in the art can be used in the present invention. Examples of particularly useful flavoring agents, include but are not limited to, lemon-lime, orange, and fruit punch. For example, the lemon-lime flavoring agent can be at a concentration in the range of from about 0.050% to about 0.200%, preferably from about 0.080 to about 0.150%, and more preferably from about 0.090 to about 0.120% by weight.

The beverage of the present invention is formulated to have an osmolality, when initially formulated, in the range of from about 220 to about 350 mOsm/Kg of beverage, and is preferably in the range of from about 250 to about 330, more preferably from about 260 to about 320 mOsm/Kg of beverage. When prepared the beverages of the present invention are isotonic. The scientific and strict definition of the term isotonic is a solution that has the same or nearly the same osmotic pressure as another solution, typically human blood. Although the beverages of the present invention can be isotonic when prepared, even with regards to the strict scientific meaning of the term, the term isotonic as presently used is not meant to be so narrowly defined. With respect to the present specification, isotonic is meant to refer to the fact that the beverages of the present invention are sports type beverages which contain a certain amount of carbohydrates and electrolytes.

The beverage of the present invention may also include a clouding agent at a concentration range of from about 0 to about 100 ppm of clouding agent. Examples of clouding agents include, but are not limited to, ester gum, SAIB, starch components and mixtures thereof, with ester gum as the preferred clouding agent at a concentration range of from about 10 to about 50 ppm and more preferably from about 15 to about 35 ppm.

The beverage of the present invention may further include citric acid at a concentration range of from about 0.24% to about 0.45% by weight. Citric acid lowers the pH in order to insure it is a high acid beverage which may be pasteurized under conditions less harsh than required for low acid beverages. Beverages of the present invention preferably have a pH of from about 2.5 to about 4.5, preferably from about 2.75 to about 4.25, more preferably from about 2.9 to about 4.0. In addition, citric acid adds tartness to the beverage.

The present invention also relates to a beverage concentrate used to prepare the beverage already described herein. As used herein, the term "beverage concentrate" refers to a concentrate that is either in liquid or gel form or in essentially dry mixture form. The essentially dry mixture is typically in the form of a powder, although it may also be in the form of a single-serving tablet, or any other convenient form. The concentrate is formulated to provide a final and complete beverage as already described herein when constituted or diluted with water or other liquid.

A preferred beverage concentrate of the present invention capable of producing the preferred beverage below when constituted or diluted with water comprises:

from about 4% to about 10% by weight of carbohydrates;
at least 30 mEq/L of beverage of sodium with a preferred range of 30-60 mEq/L;
at least 8 mEq/L of beverage of potassium with a preferred range of 8-20 mEq/L of beverage of potassium;
from about 10 to about 20 mEq/L of beverage of chloride;
from about 0% to about 0.4% of a flavoring agent;
from about 0 to about 100 parts per million (ppm) of a clouding agent; and
water wherein the osmolality of said beverage is in the range of from about 250 to about 350 mOsm/Kg. The carbohydrates can be selected from sucrose, maltose, maltodextrin, glucose, galactose, trehalose, fructose, fructo-oligosaccharides, beta-glucan and/or trioses such as pyruvate and lactate, preferably as a mixture of at least three of these. Preferably, the amount of fructose is less than the total amount of glucose from all sources of carbohydrates.

The present invention is further illustrated, but not limited by, the following examples.

EXAMPLE 1

A formulation designated as G30 was evaluated for sensory properties against four other formulations containing the typical ingredients found in commercial sports drinks. The G30 formulation consisted of a 6% carbohydrate solution in water, 30 mEq/L of sodium, 3 mEq/L potassium, about 10 mEq/L of chloride, 25 ppm of a clouding agent and 0.103% by weight of a flavoring agent. The carbohydrate solution was prepared using a mixture 3% sucrose, 1.7% glucose, and 1.3% fructose. In addition, both sodium chloride and sodium citrate were used to provide the sodium ions. The comparison formulations contained the exact ingredients except that the sodium levels of these beverages were modified so that the first formulation, designated as G0, contained 0 mEq/L of sodium, the second formulation, designated as G18, contained 18 mEq/L of sodium, the third formulation, designated as G40, contained 40 mEq/L of sodium, and the fourth formulation, designated as G60, contained 60 mEq/L of sodium.

Approximately 50 triathletes and runners completed this phase of testing. Tasting was done in a sedentary condition in a sensory laboratory. Under sedentary conditions, liking of the saltiness level and liking of the beverage overall peaked at 18 mEq/L. However, the difference between the ratings for G18 and G30 were not statistically significant. As is shown in FIG. 1, the G30 formulation had hedonic ratings which surpassed all but the G18 formulation.

EXAMPLE 2

The same formulations were used to determine the ad libitum drinking characteristics, sensory aspects, hydration characteristics, and voluntary fluid intake for each. Fifty subjects completed almost all testing and were included in the subject pool used for analyses. Of this 50, 28 were men (m age 39.7±8.0) and 22 were women (m age 37.2±9.2). For the complete pool, the average number of workout hours per week was 11.25±6.8 (range 1-35) and the average number of races participated in per year was 11.0±8.4 (range 0-35). All subjects were given dietary and exercise guidelines as follows: No heavy exercise on the day before testing. Allow at least one full day of recovery between sessions. No caffeine the day of testing. No high salt or high fat foods the evening before or the day of the testing. Do not eat within 3 hours of testing. Drink a liter of water 3 hours before testing. Void urine prior to testing.

Figure 2:
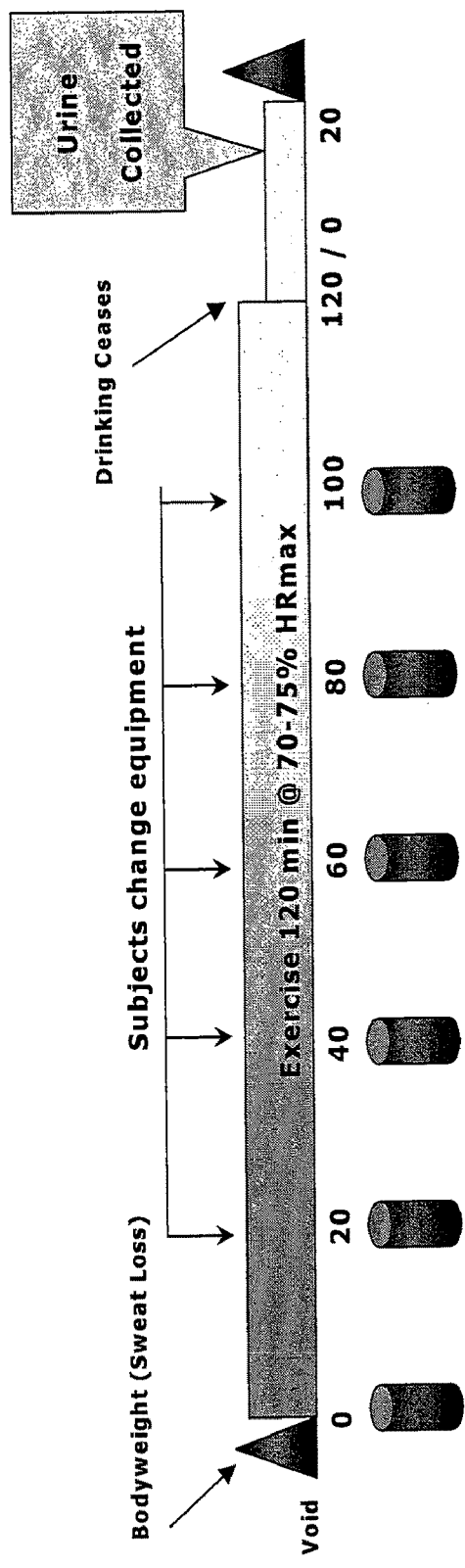
FIG. 2 illustrates the experimental procedure employed to determine ad-libitum drinking characteristics, sensory aspects, hydration characteristics, and voluntary fluid intake of various formulations.

All subjects were required to follow the diet and exercise guidelines prior to participating in the experiments. In order to assure pre-experiment hydration, 1 liter of fluid was given for each subject to finish consuming by 1.5 to 2 hours before starting the protocol. A protocol was performed to create 2 hours of moderate aerobic exercise in the heat (80° F., 36% RH, 21° C. WBGT) at 70-75% max age-predicted heart rate. Subjects were given approximately 700 ml of fluid per bottle, and they received a fresh, cold bottle each 20 minutes for the entire two hours. Subjects were allowed to drink freely until the end of exercise, at which time no further fluid was provided. All urine samples were collected during each 20-minute segment and again 15 minutes after the exercise session ended. Subjects were asked to urinate as frequently as they felt necessary, and during the protocol. FIG. 2 illustrates the procedure employed.

Figure 3:
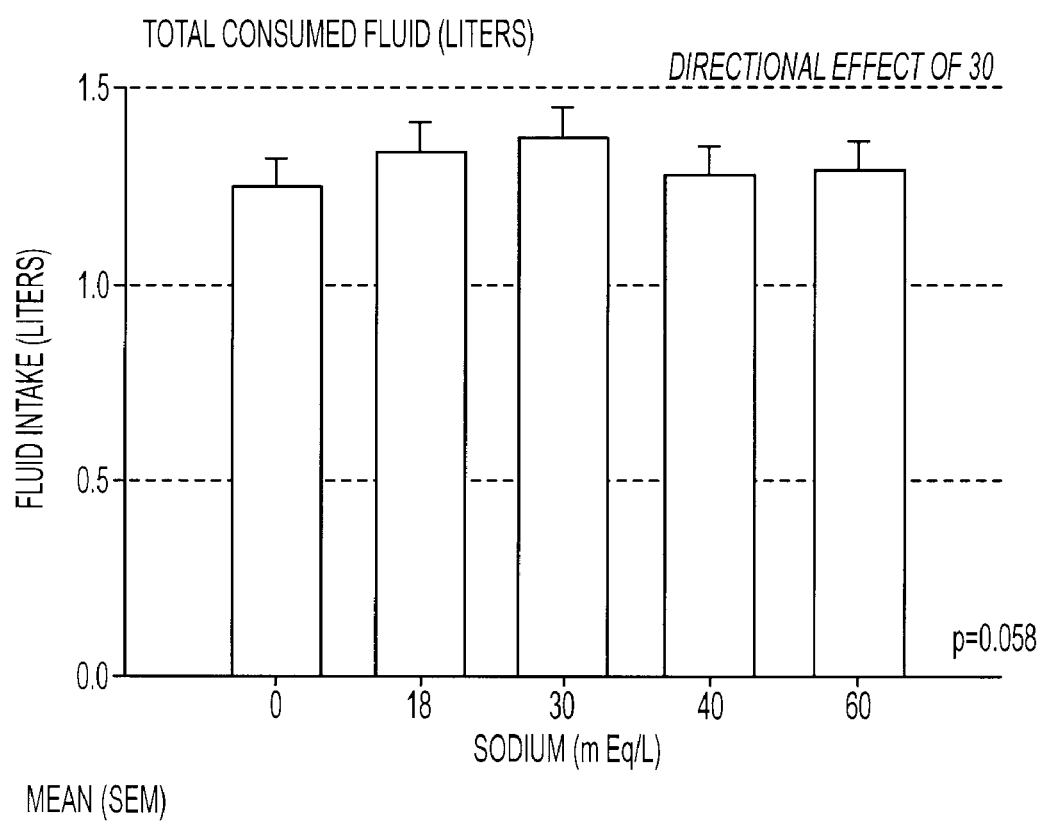
FIG. 3 shows the total fluid consumed for each of various formulations.

As the chart in FIG. 3 indicates, the total volume of fluid consumed was directionally greatest for G30 and least for G0. However, the main effect for sodium level (product) was only marginally significant (p=0.058). There was no real meaningful difference in the total voluntary fluid intake between beverages. This suggests, in part, that the subjects being athletes were well trained to drink.

Figure 4:
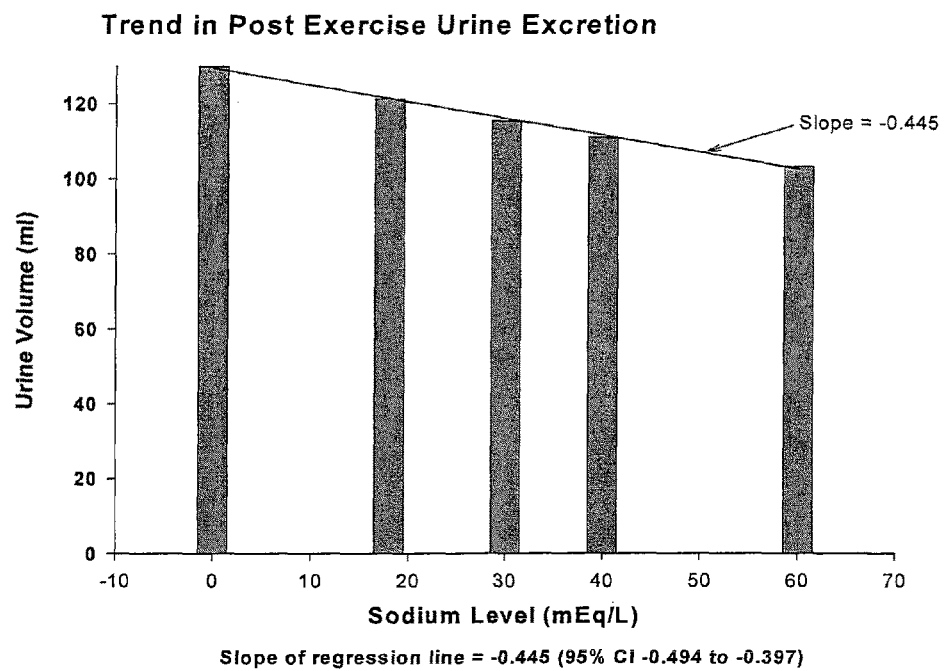
FIG. 4 shows the trend in urine loss by graphing the urine volume for each formulation.

Post-exercise urine volumes indicated an inverse association between sodium level and urine volume produced, which is indicated in FIG. 4. Urine volumes were directionally less as sodium level increased from 0 to 60 mEq/L and was least for G60 at 15 minutes post-exercise compared to other beverages. Analysis of the trend in the data (e.g. slope) for post-exercise urine excretion was significantly different from 0. That is, there is 95% confidence that the downward trend in the data was not due to chance alone. Overall, exercise urine volumes and total urine volumes were similar among beverages.

Figure 5:
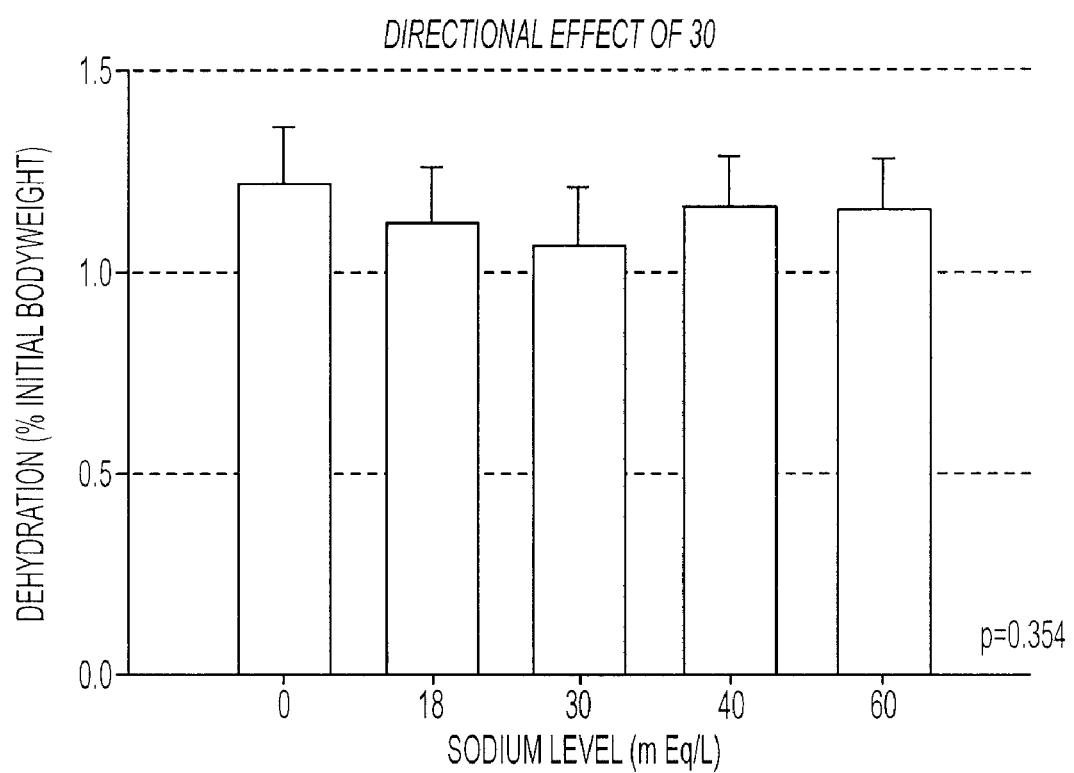
FIG. 5 shows dehydration in terms of initial body weight of individuals to whom each formulation was administered.

The level of dehydration was similar (p=0.354) among all beverages, due to the fact that all beverages were voluntarily consumed in about similar volumes. It was directionally the least for G30 at 1.06% and the most for G0 at 1.23% as shown in FIG. 5. On average, HR and RPE were not different between beverages, but did increase over time of exercise.

Overall acceptance (OA) of the beverages was greatest for G18 and G30 and differed significantly from the other beverages (p<0.05). The G18 and G30 beverages did not differ from each other with respect to OA. Liking of saltiness was greatest for G18 and G30 and was significantly different ($p<0.05$) from 0, 40, and 60 mEq/L beverages. The liking of saltiness in G18 and G30 did not differ from each other. There was also a significant interaction effect between sodium level and time. Liking of saltiness decreased over time for G0 and G18, whereas it increased for G30, G40, and G60 over time. All sodium levels were perceived to be different ($p<0.05$), increasing in perceived salt intensity as sodium level increased.

Figure 6:
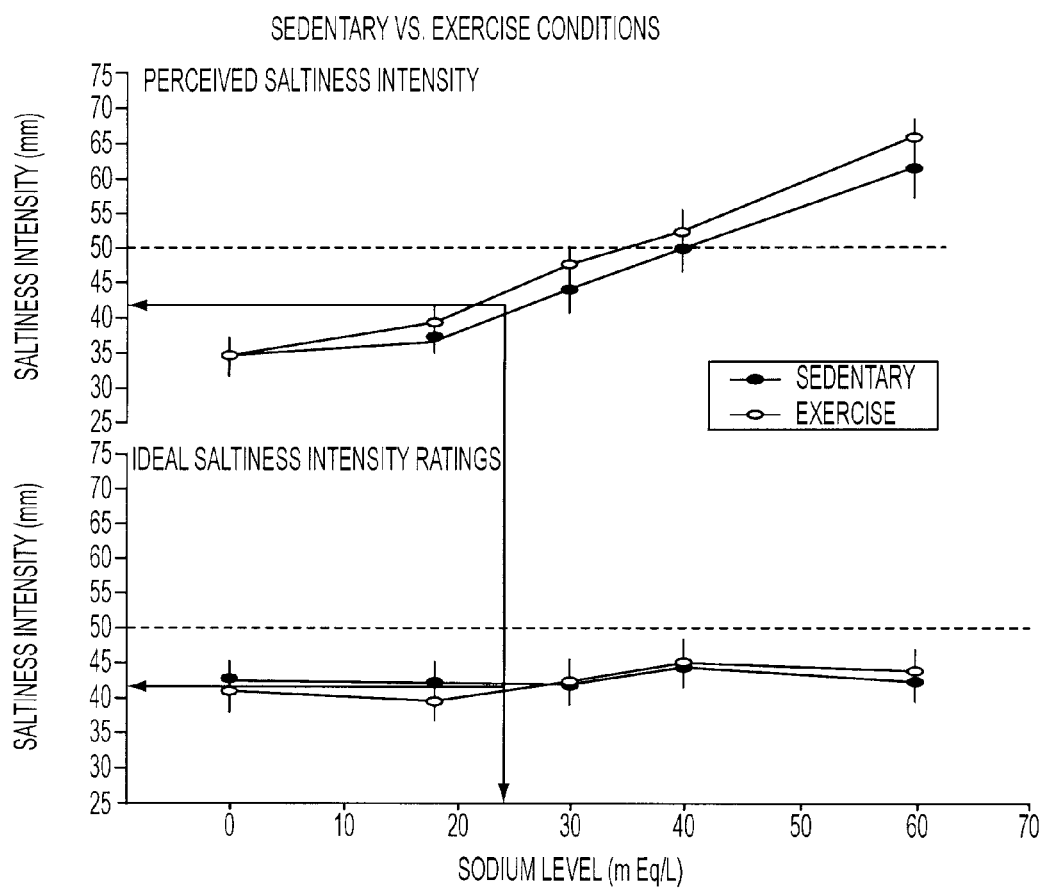
FIG. 6 illustrates the ratings of saltiness intensity during exercise and sedentary conditions and further shows the ideal perceived saltiness.

Ideal saltiness ratings were similar across all beverages, ranging from 39 to 43.5 mm (0-100 mm scale). This corresponded to a sodium level lying somewhere between G18 (38±1.5) and G30 (47±1.7). Plotting this data, ideal perceived saltiness would correspond to a sodium level of 24 mEq/L as shown in FIG. 6.

Figure 7:
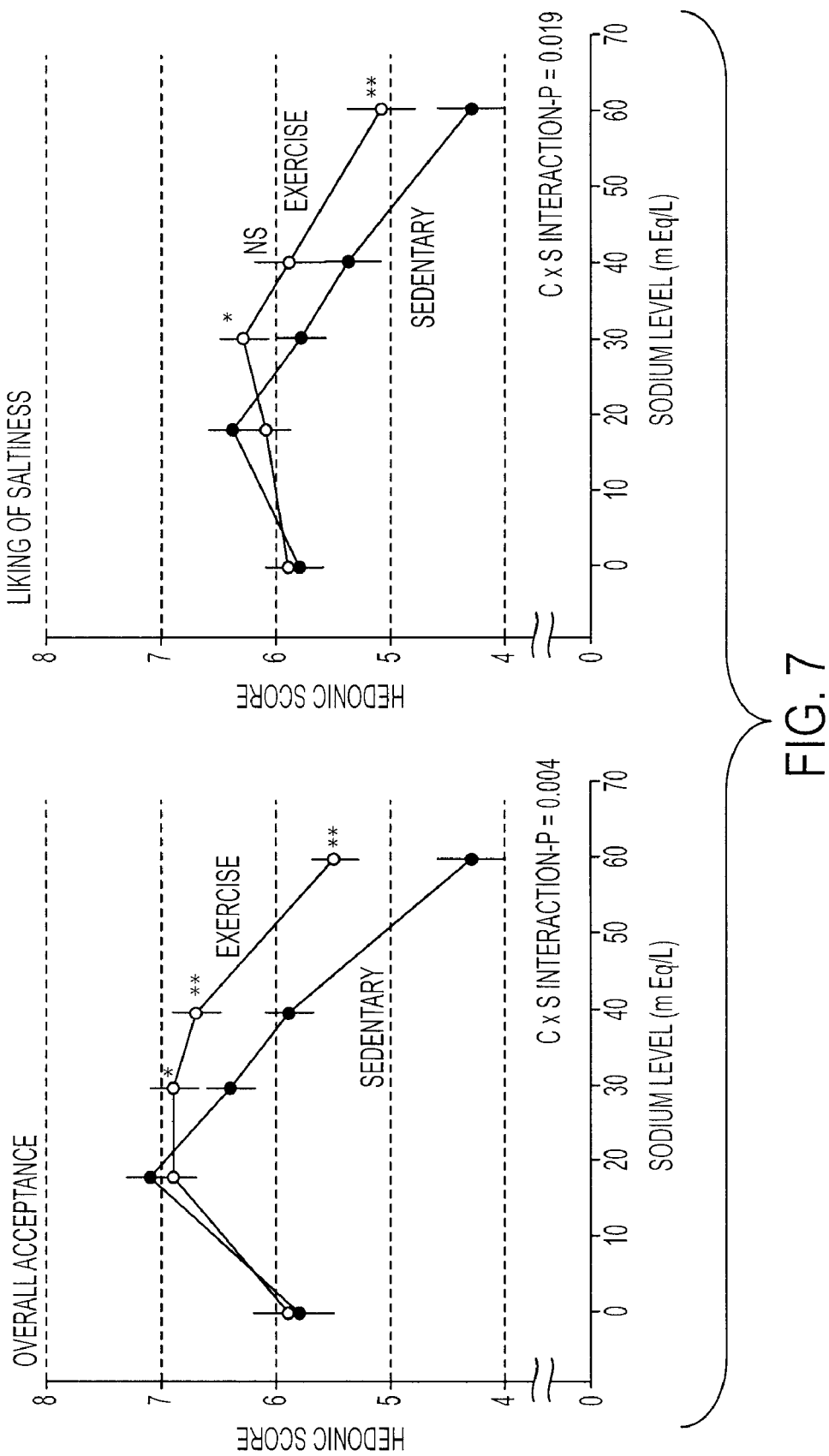
FIG. 7 shows hedonic scores in terms of overall acceptance and liking of saltiness for the various formulations during exercise and sedentary conditions.

A comparison of overall acceptance and liking of saltiness from sedentary to exercise conditions revealed a decline in the curve for OA with increased sodium level softened, meaning thus, at higher sodium levels (30, 40, 60 mEq/L), hedonic scores recorded at 60 minutes during the exercise were higher compared to the scores recorded in sedentary conditions. For liking of saltiness (LOS), the same response was observed, with the curve peak shifting from 18 mEq/L to 30 mEq/L. These results are illustrated in FIG. 7.

For both OA and LOS up to a sodium level of 60 mEq/L, hedonic scores never crossed into the "dislike" region of the scale during exercise. Ideal saltiness and perceived saltiness did not change significantly or meaningfully between sedentary and exercise conditions. There was an upward directional shift in perceived saltiness associated with the exercise condition.

The conclusions gathered from the sedentary and exercise testing indicated that moderate to high levels of sodium in G30 are not associated with any GI distress or associated symptoms during two hours of moderately intense exercise in the heat. Well-trained athletes will drink beverages that are not optimally palatable in order to preserve performance and hydration. Even though the G30 beverage is perceived to be more salty than G18, it appears that from a hedonic standpoint, 30 mEq/L of sodium is liked, is tolerable, and is even directionally favored over both higher sodium levels and no sodium in the other formulations. Acceptance is broadened and liking of sodium is increased in higher (30-60 mEq/L) sodium beverages during exercise compared to at rest.

EXAMPLE 3

This study compared all the formulations except the G40 formulation to determine how rapidly fluid is lost and how much is retained up to three hours after exercise-induced dehydration that is followed by replacement of total sweat loss. This was conducted in a double-blind experimental design with formulations counterbalanced among the study group.

Subjects were fed a standard diet for dinner (the evening prior to testing), breakfast, and lunch. The total caloric intake was 2440 calories and 2592 mg of sodium. Meals were accompanied with 500 ml of water.

All subjects were required to follow the diet and exercise guidelines prior to participating. In order to assure pre-experiment hydration, each subject was required to ingest adequate fluid. Pre-experiment hydration was further assured by checking the conductivity/osmolality of the baseline urine sample prior to the testing. Subjects whose urine sample exceeded 21 milliSiemens (mS) were dismissed from the experiment and required to reschedule.

Figure 8:
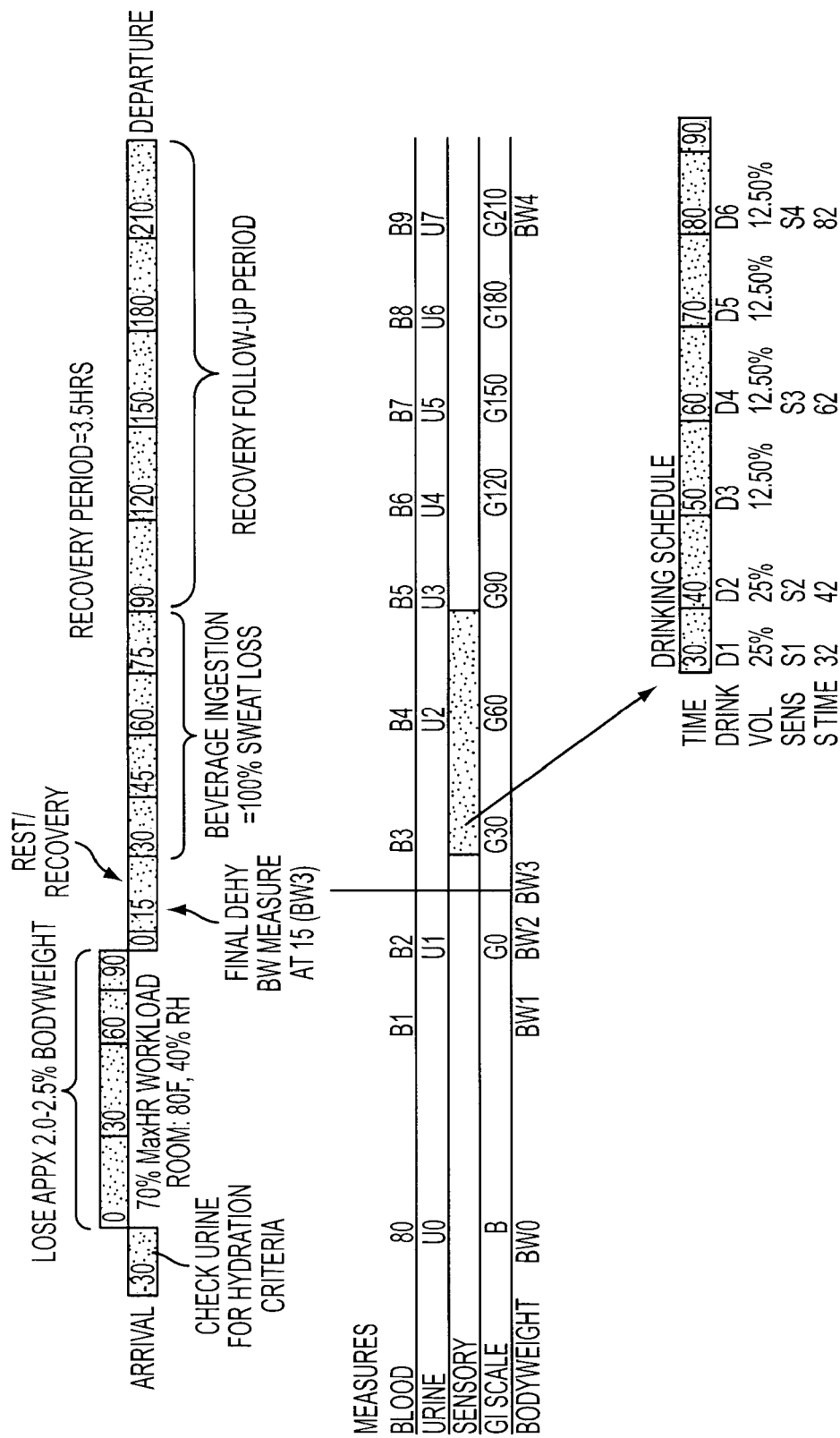
FIG. 8 illustrates the experimental protocol used to determine how much fluid is retained up to three hours after exercise-induced dehydration that is followed by replacement of total sweat loss.

Subjects were asked to complete 90 minutes of moderate-intensity cycling exercise (or enough exercise to result in a loss of approximately 2.5-3.0% of body weight) in a warm environment (80° F., 40% RH). Following exercise, they rested quietly for 3.5 hours. During the first 90 minutes of recovery, subjects drank a volume of fluid equal to 100% of their total sweat loss during the exercise-dehydration period. Over the entire five-hour period, urine samples and perceptual data were collected periodically according to the protocol. The summary of this protocol is illustrated in FIG. 8.

Ten subjects completed four trials. Average loss of body-weight during the exercise-induced dehydration was 2.6±0.6% over 1.5 hours. Dehydration did not differ across formulations.

Figure 9:
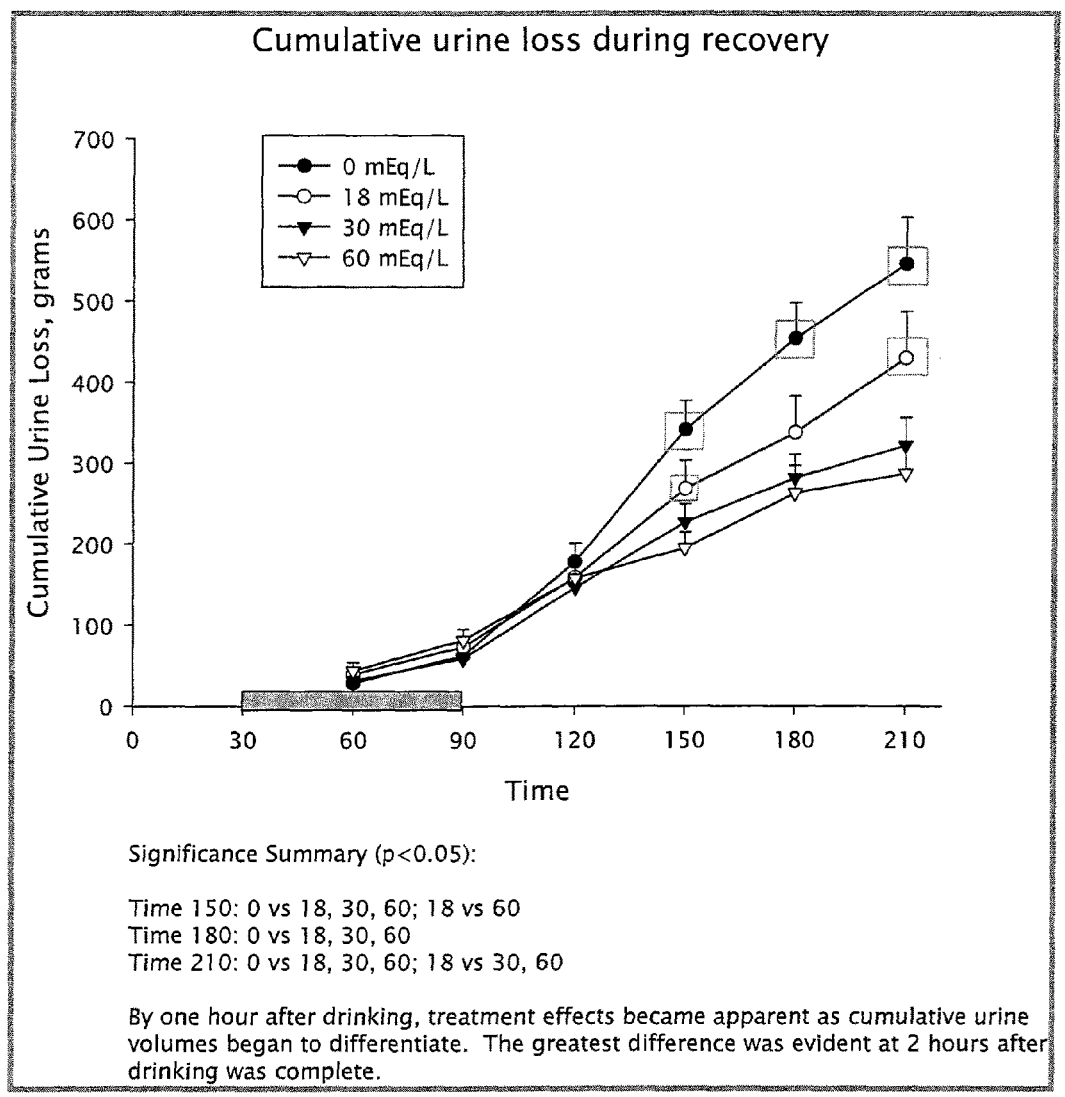
FIG. 9 shows cumulative urine loss over time during the recovery period for the various formulations.
Figure 10:
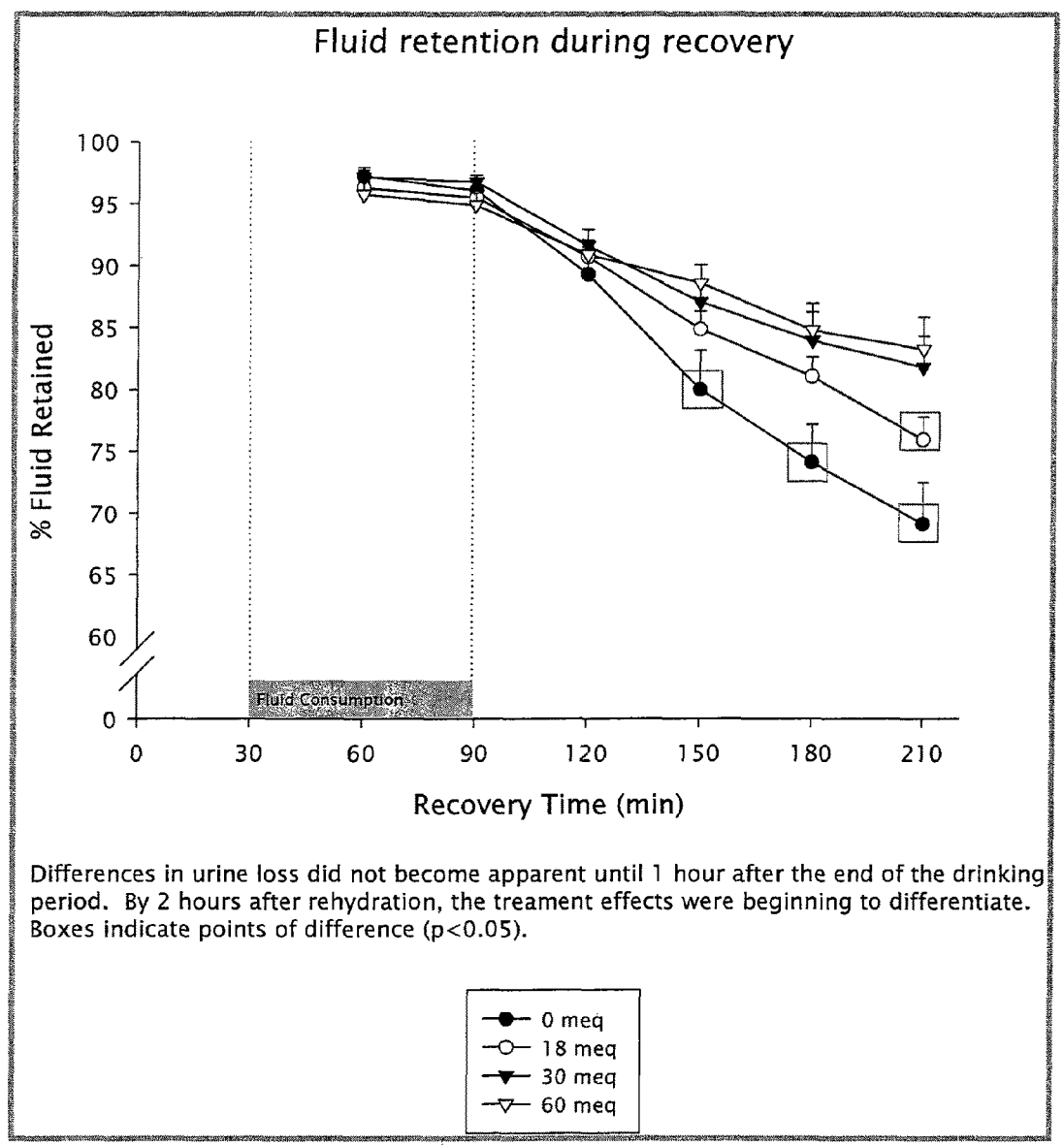
FIG. 10 shows fluid retention as a percentage of the volume ingested during recovery time for the various formulations.

At the end of the experiment, the average total urine losses were 0.546, 0.430, 0.322 and 0.287 liters for 0, 18, 30, 60 mEq/l beverages, respectively as shown in FIG. 9. Both 0 and 18 were significantly ($p<0.05$) different from 30 and 60. The 30 and 60 beverages did not differ from each other. Differences in urine loss did not become apparent until 1 hour after the end of the drinking period. By 2 hours after the drinking ended (3.5 hrs post-exercise), differences among 0, 18, and the other beverages were greatest. Average fluid intakes ranged from 1.8 to 1.95 liters, but were not different across formulations. Two hours after rehydration with a volume equivalent to 100% of total sweat lost, the total percent of fluid retained was 69%, 75%, 82%, and 83% for 0, 18, 30, and 60 mEq/L, respectively as shown in FIG. 10.

The G30 beverage scored directionally higher than all other beverages. Sensory evaluation indicated that the mEq/L was liked equally well as G18, but was directionally favored over all other beverages for characteristics of sweetness, flavor, tartness, saltiness, and overall acceptance. For the G18 and G30 beverages, ratings of perceived saltiness were very close to ideal ratings of saltiness throughout the drinking period. In general, hedonic scores declined with increasing time (30 to 90 min) during the rehydration period.

Ratings of ideal saltiness were consistent with results demonstrated in Example 2 (n=50), but were slightly higher (43-50 vs. 40-42). In most cases, perceived saltiness for the G30 beverage was scored near to ideal saltiness ratings for that beverage. As consumption continued past 60 minutes, perceived saltiness levels of the beverages became less than ideal. The variation between perceived and ideal saltiness was greater for the G0 and G60 formulations, than for control G18 or G30.

There were no marked differences in perceived alertness, energy, GI assessments or well-being among the four beverage trials.

The G30 formulation performed directionally better than G18 for a number of hedonic ratings and provided a greater fluid retention response during rehydration than other beverages. The highest sodium level in the G60 formulation provided no further benefit beyond the G30 formulation in terms of attenuating fluid loss in the form of urine.

The conclusions gathered indicate that G30 provides the following advantages over G0, G18, G60: (1) directionally higher hedonic ratings in athletes undergoing exercise in the heat and (2) attenuated urinary fluid losses after rehydration with a volume equivalent to 100% of sweat loss.

EXAMPLE 4

The same formulations as Example 3 were used except that a G5 formulation was included and the G0 and G60 formulations were eliminated. The G5 formulation was identical to the other formulations except that the sodium level was adjusted to 5 mEq/L.

This testing compared the formulations to determine how rapidly fluid is lost and how much is retained up to three hours after exercise-induced dehydration that is followed by replacement of total sweat loss. Certain biochemical parameters were measured to determine physiology related changes. The parameters measured were blood related changes in [Na+], [K+], [Ca++], osmolality, Hb, Hct, ΔPV, glucose, pH, and urine related changes in volume, osmolality, [Na+], [K+], SEC, FWC, creatinine, and GFR. This was also conducted in a double-blind experimental design with formulations counterbalanced among the study group.

Seventeen (n=17) male subjects dehydrated by 2.25±0.61% of bodyweight during 1.5 hours of cycling at 70% of maximum heart rate in a warm (80° F., 40% RH) environment. Subjects were fed a standard diet for dinner the evening prior to testing, and for breakfast and lunch the day of the test. The total caloric intake was 2440 calories and 2592 mg of sodium. Additional liquids (within guidelines) were permitted until 3 hours prior to the testing.

In order to assure pre-experiment hydration, each subject was required to ingest fluid adequate to establish euhydration. This included a minimum intake of 500-ml of water the evening prior to the test as well as 1-liter of water the day of the test. Pre-experiment hydration was further assured by checking the conductivity of the pre-experiment urine sample prior to the experiment. Subjects whose first experimental urine sample had a conductivity that exceeded 21 mS-cm were dismissed from the experiment and required to reschedule. An indwelling venous catheter was inserted into a forearm vein for repeated blood sampling throughout the experiment.

Subjects cycled in a warm environment (80° F., 40% RH) for 1.5 hours to elicit an exercise-induced dehydration near two percent of initial bodyweight. A previously determined workload was used to set an exercise intensity equivalent to 70-75% of maximal heart rate as determined by earlier maximal treadmill tests. Heart rate was monitored every 10 minutes using a telemetered HR monitor (Polar) and to assure sufficient intensity of exercise.

At 1-hour, subjects were allowed a 5-minute break from cycling during which time a dry weight was measured to determine sweat loss progress. At the end of the exercise-dehydration period, a 15-cc pre-recovery blood sample was taken while upright on the bike, and subjects urinated and were weighed again to determine final sweat loss. The subjects were then seated in a reclined position for the remainder of the recovery period. Where appropriate, the subject's arm containing the indwelling catheter was wrapped in a heating pad to maintain blood flow and vessel dilation that provided for better blood sampling in a dehydrated state.

Beverage was mixed prior to the experiment using 1-liter and 2-liter volumetric flasks and beverage grade water that did not contribute any electrolytes to the beverage. Beverages were served chilled from the refrigerator (approx. 40° F.), although the last two beverages were likely to be closer to ambient temperature by the time they were served to the subjects.

At 30 minutes into recovery, subjects received their first of six cups of beverage, followed by another cup every ten minutes. Total beverage volume was equivalent to total sweat loss, and was portioned such that subjects received 50% of the total volume in the first 20 minutes and the remaining 50% in 12.5% portions every ten minutes for the remaining 40 minutes. All fluid was consumed within an hour.

Figure 11:
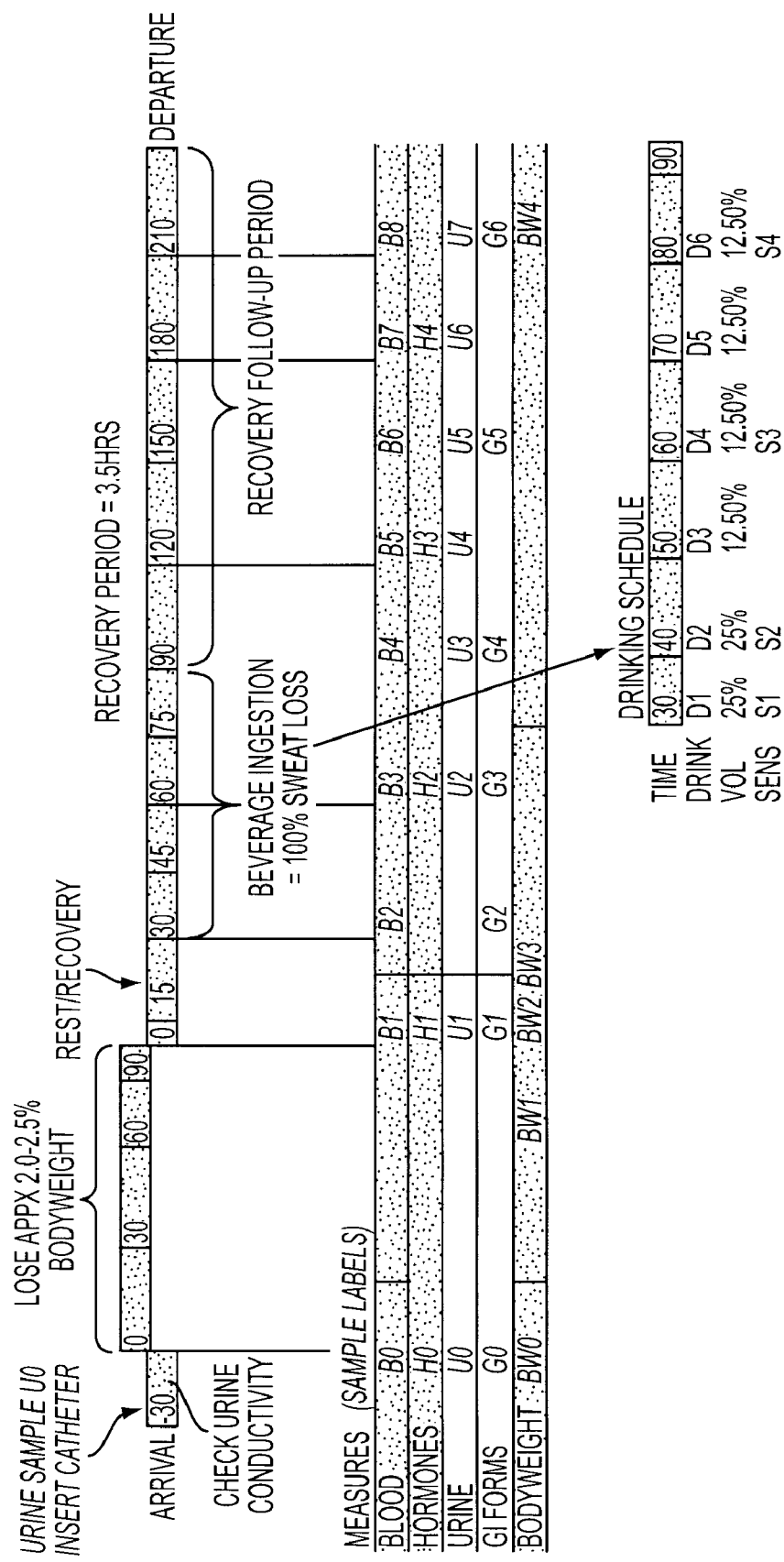
FIG. 11 illustrates the experimental protocol used to determine how much fluid is retained up to three hours after exercise-induced dehydration that is followed by replacement of total sweat loss.

Every 30 minutes during the 3.5 hour recovery, blood and urine samples were taken. The testing protocol and sequence are shown in FIG. 11.

A whole blood clinical analyzer (Instrumentation Laboratories, Synthesis IL1735) was used to measure changes in blood sodium, potassium, ionized calcium, glucose, hematocrit, hemoglobin, and pH value. Approximately 1-ml of whole venous blood was collected in a 3-ml heparinized arterial blood-gas syringe (Marquest, GASLYTE) and was used specifically for the clinical analyzer. The arterial blood gas syringe was chosen to avoid sample clotting and to ease presentation of the sample to the clinical analyzer.

Plasma volume changes were estimated from a published equation (Dill/Costill) relating hematocrit and hemoglobin changes. Plasma osmolality was measured by freezing point depression method on a FISKE 2400 multiple sample osmometer.

Urine volume was determined by weight, and urine conductivity was immediately determined using a conductivity meter (WTW LF 340, model 19706-20). Urine was then aliquoted and stored at −20° F. until later analysis for [Na+], [K+], osmolality and creatinine. Urine [Na+] and [K+] were determined using flame photometry (IL943 Automatic Flame Photometer) after centrifuging for 15 minutes to remove any insoluble particles from the sample to be analyzed. Urine creatinine was determined on the spectrophotometer utilizing a Sigma Creatinine Kit (Sigma Diagnostics, No. 555). Urine osmolality was determined by the freezing point depression method on an osmometer after thawing frozen samples to room temperature.

Data were analyzed using a computer statistics package (SPSS, v.10). Descriptive statistics and summary tables were generated for all dependent measures. Repeated measures ANOVA was used to test for main effects of treatment and where appropriate time dependent effects. Where main effects existed, a Duncan post-hoc test was used to determine statistical differences among means. Comparisons were tested with an alpha level equal to 0.05. Effect size estimates were made for comparisons of total urine loss between formulations.

Seventeen subjects (N=17) completed all three trials, with the exception of one subject who became ill (unrelated to the study), but was forced to discontinue the study after already completing two trials. Average loss of bodyweight during the exercise-induced dehydration was 2.25±0.61% over 1.5 hours. The subjects exhibited an average sweat rate of 1.2±0.3 liters/hr and lost an average of 1.7±0.5 liters of sweat during the dehydration period. Dehydration and sweat loss did not differ across formulations.

Figure 12:
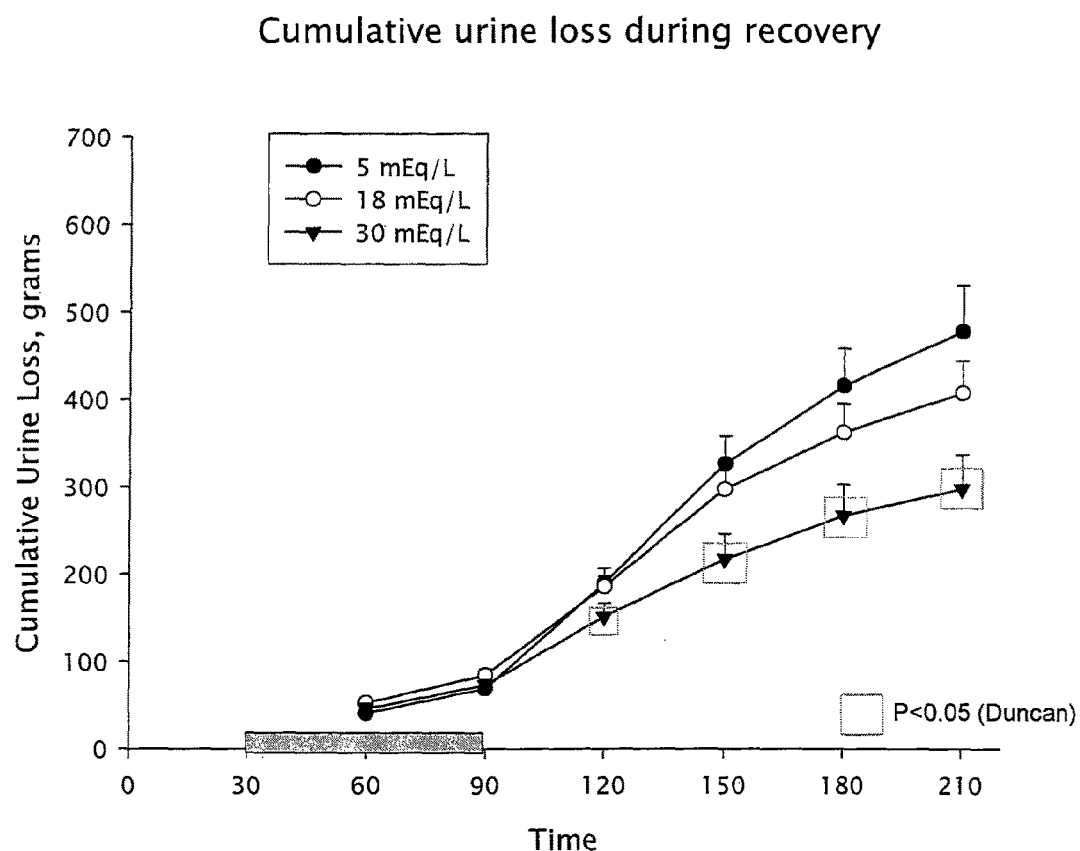
FIG. 12 shows cumulative urine loss over time during the recovery period for various formulations.

During the recovery period, total urine loss was significantly lower for G30 (298±161 g) compared to G5 (479±209 g) and G18 (408±151 g) formulations, but this effect was time dependent. It was not until 120 minutes in recovery (30-min post-drinking) did the effect of G30 become different from G5 and G18. FIG. 12 shows cumulative urine loss among the three formulations across recovery time. Effect sizes estimates for total urine loss were 0.39 (G5 vs. G18), 0.97 (G5 vs. G30), and 0.70 (G18 vs. G30).

Figure 13:
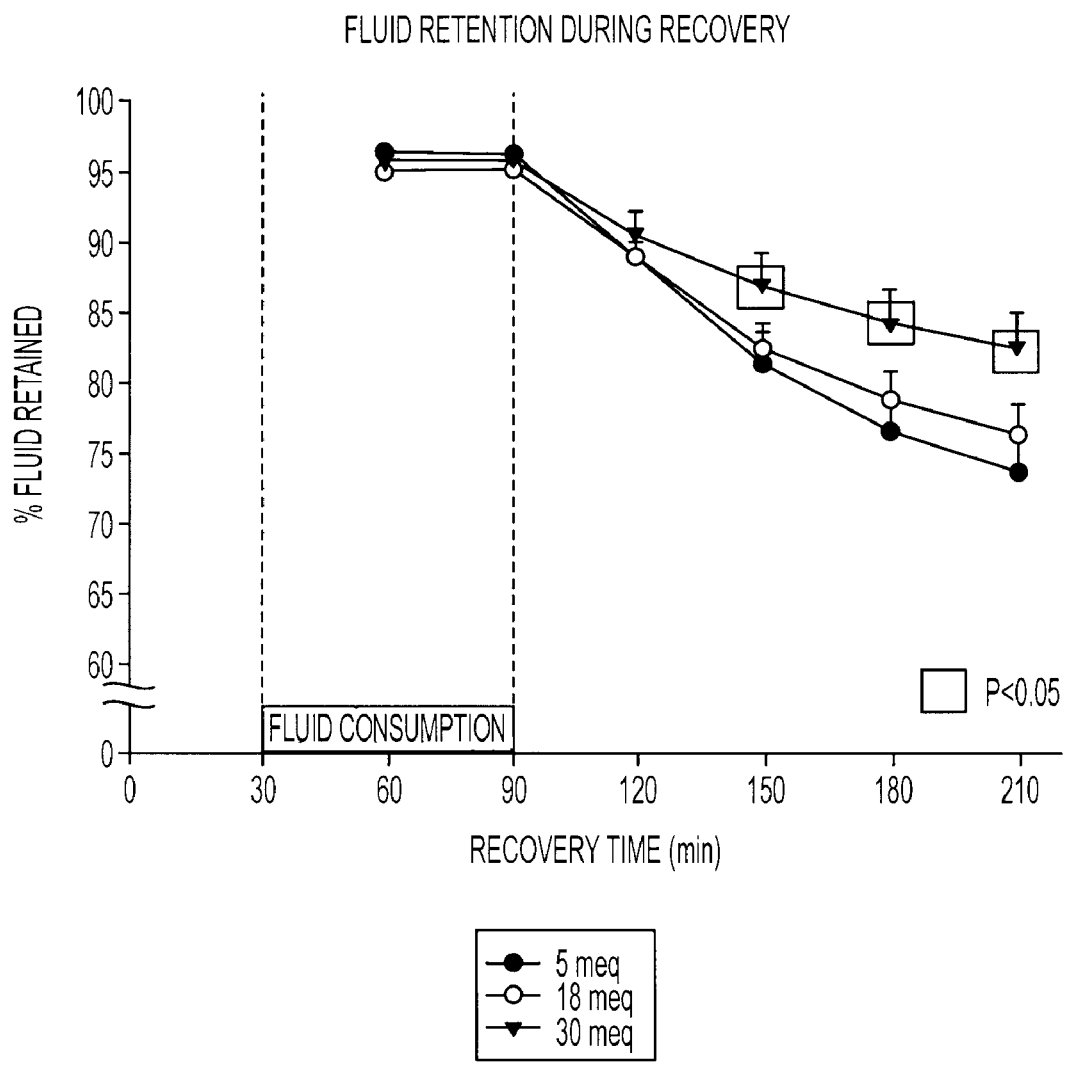
FIG. 13 shows fluid retention as a percentage of the volume ingested during recovery time for various formulations.

Percent of fluid retained was significantly higher (P<0.05) for G30 versus G5 and G18 at 150 through 210 minutes in recovery. Thus, at the end of the recovery period (2 hours post-consumption), fluid retention was 72.6%, 75.2%, and 81.6% for G5, G18, and G30, respectively. FIG. 13 shows fluid retention during recovery for the three formulations tested.

Absolute change in bodyweight from baseline weight was significantly greater for G5 compared to G18 and G30 (P<0.05). Bodyweight losses, corrected for any fluid gains during recovery, were 0.93, 0.80 and 0.74 kg, respectively.

Figure 14:
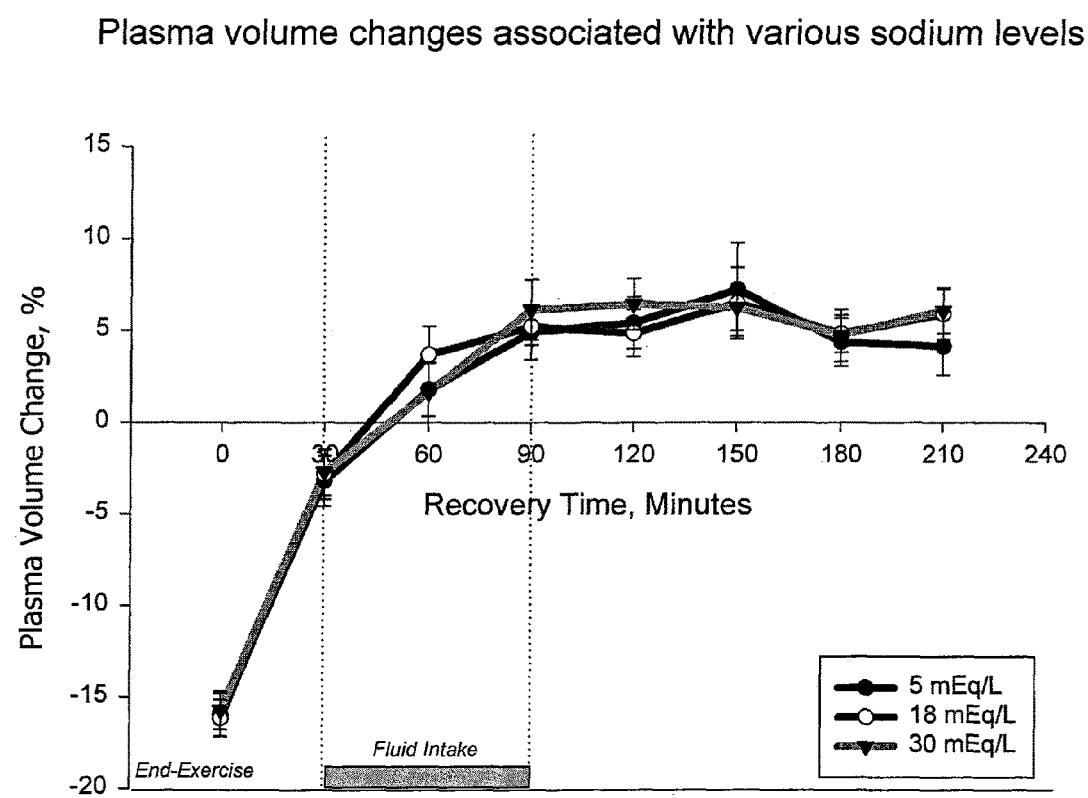
FIG. 14 shows the plasma volume changes over time for various formulations.

There were no treatment effects on plasma [Na+], [K+], [Ca++], or glucose. Additionally, change in plasma volume (DPV) as calculated from hematocrit and hemoglobin was not different among the three formulations. Change in plasma volume among the three formulations is shown in FIG. 14.

ANOVA analysis revealed a main effect of sodium (P<0.001) and time (P<0.0001), with an interaction between sodium and time (P<0.0001) on individual urine volumes excreted. Independent of time (summed across time points), average urine volumes were 79.8, 68.0, and 49.7 g for G5, G18, and G30, respectively.

Urine conductivity varied by sodium level and time, with an interaction between sodium and time (P<0.01). Independent of time (summed over all time points), average urine conductivity was 12.3, 12.8 and 14.8 mS-cm for G5, G18, and G30, respectively. Conductivity was significantly higher for G30 compared to G5 and G18.

Urine sodium and potassium concentrations were not different between sodium levels, but did differ by time. Urine sodium and potassium excretion, corrected for volume, did not differ between formulations, but did differ over recovery time. When summed across formulations, average [Na+] excreted was significantly higher at 0 minutes recovery (7 mEq), dropped to 4.4 mEq at 30 minutes into the drinking period, and remained between 2.2-2.4 mEq from 90 through 210 minutes of recovery.

To examine any sensory (taste) and perceptual changes associated with the various formulations, the subjects rated a number of psychophysiological characteristics on several different scales (e.g. categorical, 100 pt) throughout the experimental period.

Overall acceptance of beverages was not significantly different among formulations. The G30 beverage significantly declined in overall acceptance, and liking of flavor, saltiness, sweetness, and aftertaste, particularly at the end of the 1-hr drinking period. Acceptance of the G5 and G18 products did not decline over time. There were no differences in perceived saltiness between G5 and G18, but G30 was perceived to be saltier at two of the four evaluation times (32 and 62 minutes). The effect was not consistent.

Beverage treatment had no effect on ratings of ideal saltiness as ideal saltiness consistently ranged from 47 to 51 pts on a 100-pt scale. Perceived saltiness did not differ from ratings of ideal saltiness for G5 and G30, but G18 was rated significantly less salty than ideal at both 32 and 62 minutes. Again, this effect was not consistent across time.

There were no differences in perceptions of physiological or psychological well-being among formulations. Perceived energy, alertness, and feelings of well-being were similar with all formulations, but did vary over time consistent with the experimental protocol. At the end of the experiment, the G30 product resulted in significantly lower ratings for hunger compared with G5 and G18. There were no other treatment effects on any of the ratings of perceived gastrointestinal stress (bloating, fullness, nausea, or urge to urinate).

Although there were no differences in perceived thirst among products, subjects consuming the G18 product were directionally more thirsty than those consuming either G5 or G30.

EXAMPLE 5

For the same purposes as the Example 4, the G30 formulation was compared to water (W), a commercial product POWERade® (P), and a G18 formulation identical to the G30 formulation except that the sodium level was adjusted to 18 mEq/L. Specific electrolyte formulations are shown below.

| Code | [Na$^+$], mEq/L* | [K$^+$], mEq/L* | [Cl$^-$], mEq/L | Osm (mOsm/kg)* |
|------|------------------|-----------------|-----------------|----------------|
| W | 0 | 0 | 0 | 0 |
| P | 5 | 2 | 5.8 | 428 |
| G18 | 18 | 3 | 9 | 320 |
| G30 | 30 | 3 | 9 | 334 |

*Indicates measured analytical values

Beverage temperature was maintained between 41-45° F. and served at that temperature and the beverages were blinded to the subjects as well as the experimenters.

Subjects included trained men (ages 25-50 y). Seventeen completed both trials. Testing followed a 3-hour fast (drinking and eating).

Workloads were set for the cross-trainer, stationary bike and treadmill sufficient to produce intensities between 70-75% of their measured maximum heart rates (determined from annual stress tests). In addition, body weights were obtained prior to and following the orientation exercise session in order to predict sweat rates.

Subjects were provided with standardized meals to ensure consistent sodium intake (~2900 mg) prior to each of the two trials. Meals included dinner (evening prior to experiment), and breakfast and lunch on the day of testing. Subjects were given the option of eating all or a portion of the food provided but were instructed to record which foods and amount left uneaten. These items were then withheld from the food bags for the next trial. In addition, they were given bottled water to drink the evening before (500 ml) and during the testing day (1000 ml) to ensure adequate hydration. Subjects were asked to refrain from caffeine and alcohol use for 24-hours prior to the experiment. Most subjects ate all the food provided to them, however, intakes ranged from 2,109-2,278 kcal and 2,849-2,960 mg sodium. None of the subjects ate food other than what was provided.

The exercise session consisted of 30-minutes each on the cross trainer, stationary bike and treadmill at 75-80% maximum heart rate for a total of 90 minutes. Heart rates were taken at 15-minute intervals to ensure subjects maintained adequate intensity. Subjects refrained from drinking during the entire exercise period in an effort to produce 2-2.5% dehydration.

Following exercise, subjects were weighed and gave a post-exercise urine sample, followed by a 3.5 hour recovery period. At 30 minutes into recovery, subjects were given their first beverage equivalent to 25% of their total sweat loss (determined by subtracting post-exercise weight from pre-exercise weight). A beverage (25% of losses) was given again at 40 minutes into recovery. The third aliquot of beverage, equivalent to 12.5% of sweat loss, was given at 50 minutes. At 58 minutes, subjects were given a GI scale to assess gastrointestinal responses and a urine sample was taken. After which they were given their fourth aliquot (12.5%). The fifth aliquot (12.5%) was given at 70 minutes, and the sixth and final aliquot (12.5%) was given at 80 minutes. Sensory questionnaires were filled out periodically. At 90, 120, 180 and 240 minutes, GI scales were given and urine samples were collected. After the final urine sample, final body weights were measured.

Urine volume was determined by weight and urine specific gravity was measured (A 300 Clinical Refractometer). Urine was the transferred into 4-ml cryovials for further analysis. Urine [Na+] and [K+] were determined using flame photometry (IL943 Automatic Flame Photometer) after centrifuging for 15 minutes to remove any insoluble particles from the sample to be analyzed. Osmolality was measured for each sample (Fiske 2400 Osmometer).

SPSS version 10.0 was used to analyze the data. ANOVA using a general linear model was used to determine differences among mean values. Data is reported as the mean+the standard deviation.

The 90-minute exercise session resulted in similar levels of dehydration among formulations (2.67±0.63%, 2.71±0.64%, 2.61±0.43%, and 2.61±0.54% for W, P, G18 and G30, respectively). In addition, sweat rates among formulations were essentially the same (1.34±0.40 L/hr, 1.36±0.38 L/hr, 1.25±0.28, 1.30±0.33 L/hr W, P, G18 and G30, respectively).

Total fluid intake among formulations was also similar between trials at 2.01±0.60 L for W, 2.03±0.57 L for P, 1.88±0.41 L for G18 and 1.95±0.50 L for G30. The volume administered varied slightly in mean value because of the modest variability in sweat rate and the protocol of replacing 100% of the total sweat losses.

Final body weights as percentage of initial body weights differed among formulations. Subjects returned to 98.45±0.29% of initial body weight following the water trial, significantly less than the other three formulations. POWERade® (98.72±0.37%) and G18 (98.87±0.28%) were not different from each other. In addition, G18 was not different from G30 (98.97±0.39%). G30 was significantly different from water and POWERade®.

Total cumulative fluid output was significantly different among formulations. W resulted in significantly more urine loss than the other three formulations (0.726±0.225 L). P and G18 were not significantly different from each other at 0.496±0.184 L and 0.428±0.196 L, respectively. G30 was different from W and P, but not from G18 (0.367±0.263 L). Urine output at each data collection point was not significantly different among formulations for time points 60, 90 or 120. However, at time point 180, W resulted in greater urine loss compared to the other three formulations. Additionally, at time point 240, W and P resulted in greater urine loss than G18 and G30 (See TABLE I, values being reported in milliliters collected at each of the time points.)

TABLE I

| Treatment | 60 minutes | 90 minutes | 120 minutes | 180 minutes | 240 minutes |
|---|---|---|---|---|---|
| Water | 40.72 ± 24.95 | 35.32 ± 22.46 | 115.94 ± 55.65 | 349.39 ± 152.72* | 184.77 ± 122.51^ |
| POWERade ® | 38.29 ± 26.86 | 32.75 ± 22.51 | 76.45 ± 54.42 | 182.16 ± 84.43 | 166.08 ± 107.67^ |
| G18 | 49.73 ± 42.37 | 30.68 ± 21.71 | 100.75 ± 62.70 | 151.57 ± 93.18 | 95.07 ± 59.40 |
| G30 | 35.05 ± 25.26 | 24.30 ± 15.42 | 82.21 ± 72.17 | 133.14 ± 153.26 | 92.07 ± 69.09 |

Each time point represents the number of minutes into recovery.
*Denotes significantly more urine loss than P, G18, and G30.
^Denotes significantly more urine loss than G18 and G30.

Figure 15:
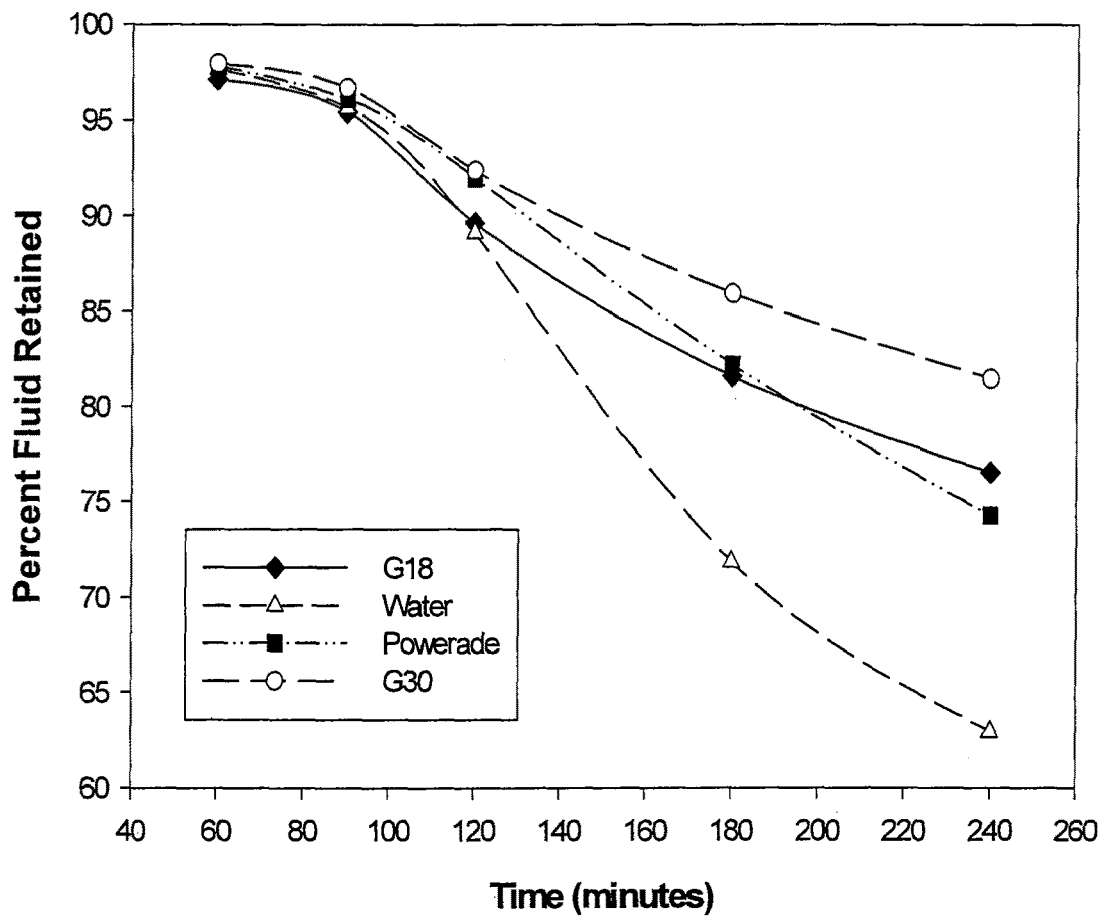
FIG. 15 shows fluid retention as a percentage of the volume ingested during recovery time for various formulations.

Fluid retention, or the amount of fluid consumed that was not excreted as urine, was different among formulations. This was calculated in both relative terms (ml/kg) and as a percentage calculated as (fluid in-fluid out)/fluid in. Relative fluid retention for W was 17.07±5.22 ml/kg, significantly less than the other formulations. P, G18, and G30 were 20.43±6.50 ml/kg, 19.48±4.83 ml/kg, and 21.26±4.83 ml/kg, respectively. Percent fluid retained was different among formulations (62.94±9.05% for W, 74.25±11.15% for P, 76.52±10.32% for G18, and 81.45±10.34% for G30) with W significantly less than P, G18 and G30 at minutes 180 and 240. Additionally, fluid retention was significantly greater in the G30 trial compared to W and P at the end of recovery (minute 240). G18 was not different from P or G30. See FIG. 15.

Figure 16:
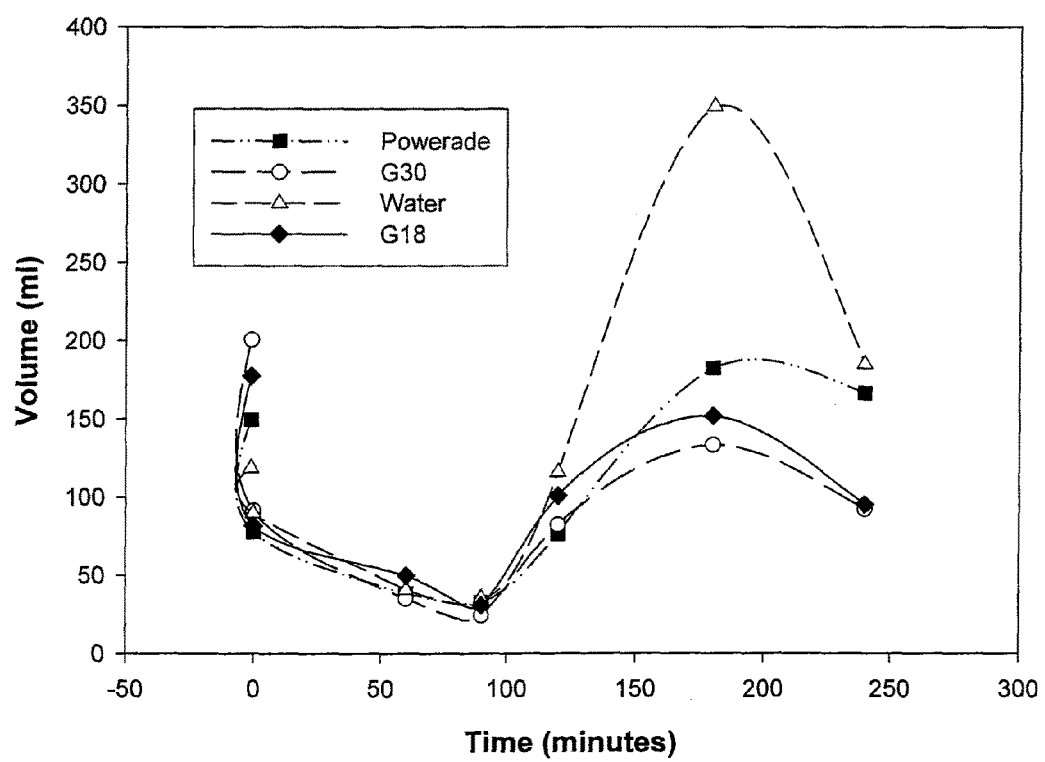
FIG. 16 shows urine production over time during a recovery period for various formulations.

Urine produced during the recovery period was different among formulations. As depicted by FIG. 16, W (x=134.97 ml) was significantly different (greater urine volume) than P (x=98.99 ml), G18 (x=91.64 ml) or G30 (x=86.38 ml). G30 resulted in significantly less urine production than W and P. G18 was not different than P or G30. See FIG. 16.

Figure 17:
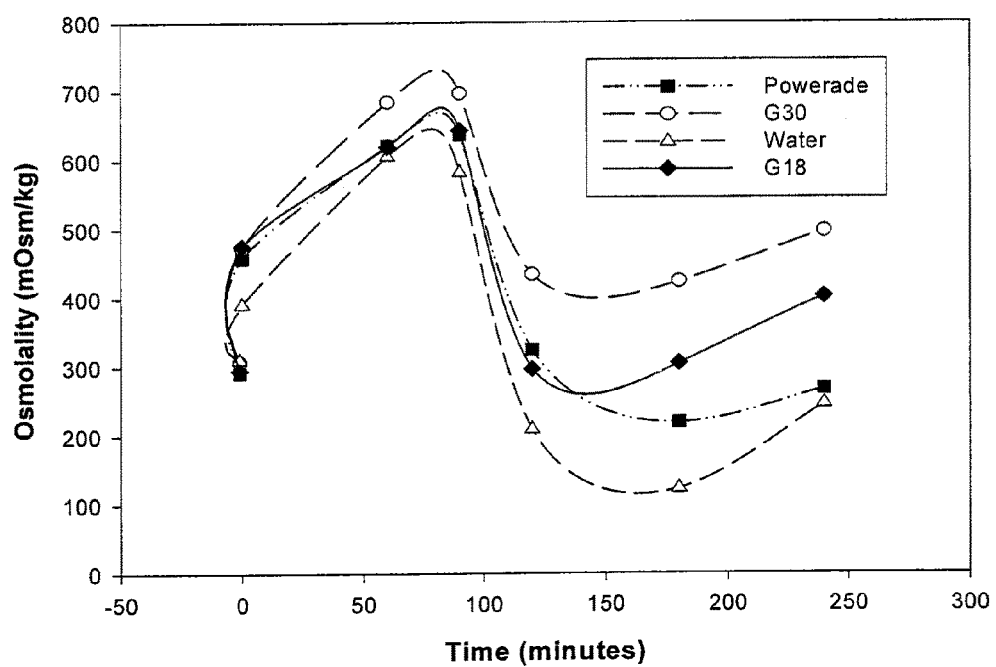
FIG. 17 shows the urine osmolality over time—before exercise and during recovery—for various formulations.

Average urine osmolality was different among formulations. W resulted in the lowest urine osmolality (348.33 mOsm) and was not different from P (400.66 mOsm) but was significantly different from G18 (431.74 mOsm) and G30 (500.42 mOsm). G18 was not different from P or G30. P was significantly less than G30. See FIG. 17.

Figure 18:
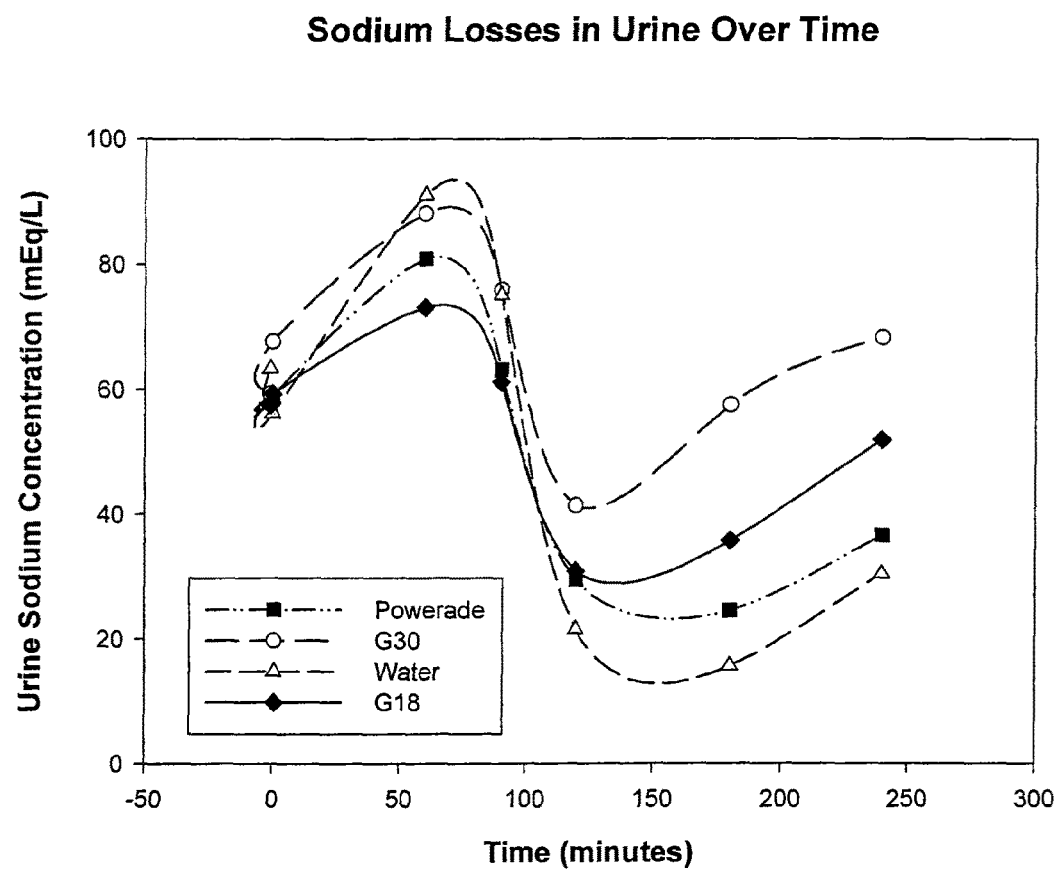
FIG. 18 shows urine sodium losses over time for various formulations.

Average urine sodium concentration was significantly greater for the G30 trial (65.19±45.68 mEq/L) compared to the other trials (W=49.73±39.78; P=50.14±41.93; G18=52.48±40.44). None of the other trials were different from each other. See FIG. 18.

Figure 19:
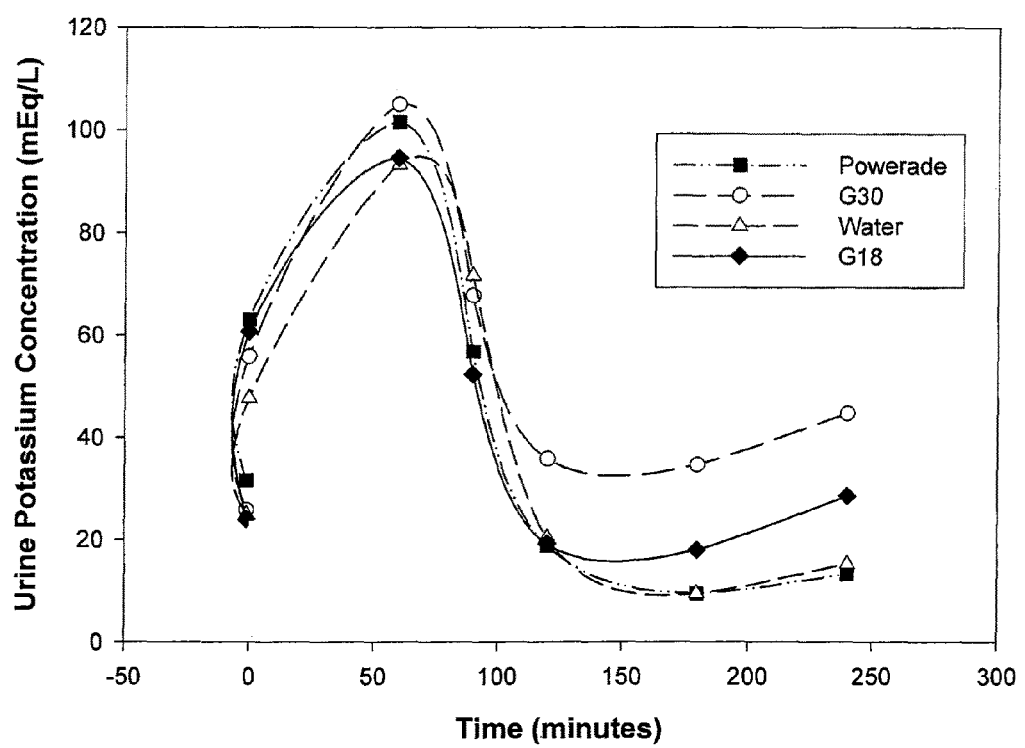
FIG. 19 shows urine potassium losses over time for various formulations.

The G30 trial resulted in significantly more potassium loss (52.25±36.56 mEq/L) compared to the other trials (W=39.67±38.15; P=41.82±40.42; G18=41.58±33.97). The other trials did not differ from each other. See FIG. 19.

Figure 20:
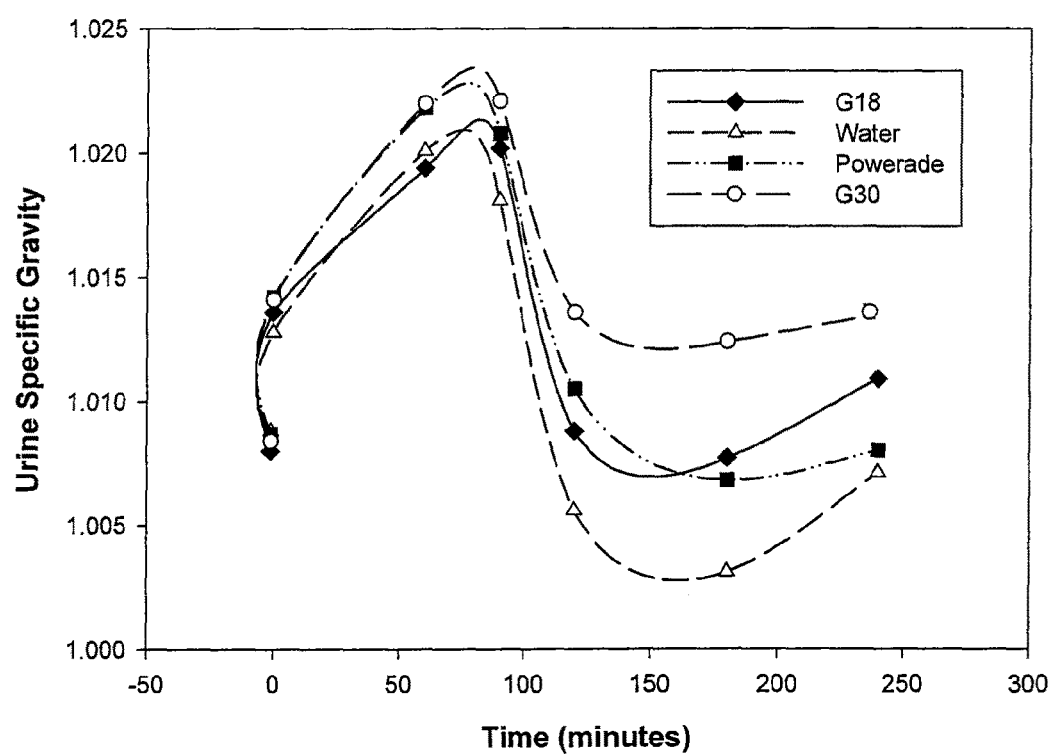
FIG. 20 shows urine specific gravity over time for various formulations.

Subjects began each exercise session well hydrated (USG=1.008±0.005). Urine specific gravity did not differ among formulations prior to exercise. Average USG for W treatment was significantly less than P at minute 120. Additionally W was less than G18 and G30 at minute 180. USG for P was significantly less than G30 at minutes 180 and 240. G18 and P were not different from each other at any time point. See FIG. 20.

The estimated acute sodium balance is shown in TABLE II.

TABLE II

| | Intake | Out (mEq) | | Estimated Total | Percent |
|---|---|---|---|---|---|
| | (mEq) | Sweat* | Urine^ | Loss | Replaced |
| Water | 0 | 131.15 | 15.51 ± 7.11 | 146.66 | 0 |
| POWERade ® | 10.19 | 132.80 | 13.52 ± 9.42 | 146.32 | 6.96 |

TABLE II-continued

| | Intake | Out (mEq) | | Estimated Total | Percent |
|---|---|---|---|---|---|
| | (mEq) | Sweat* | Urine^ | Loss | Replaced |
| G18 | 33.86 | 122.58 | 15.65 ± 9.95 | 138.23 | 24.50 |
| G30 | 58.59 | 127.24 | 14.79 ± 8.88 | 142.03 | 41.25 |

*Sweat losses estimated from an average of sweat patches placed on each forearm during one of the four exercise sessions. The amount was calculated by multiplying concentration by volume of sweat lost for a given night.

^Cumulative loss determined from the sum of the concentration of sodium in each urine sample multiplied by the volume of each sample. No differences were found in mean urine sodium loss between formulations.

Urine protein was measured via reagent strips (Uristix) to determine whether or not dehydration has an effect on protein excretion. TABLE III is a chart indicating the frequency and amount of protein detected in the urine at each time point for each of the four formulations.

TABLE III

| Time | Protein (mg/dl) | Water | POWERade® | G18 | G30 |
|---|---|---|---|---|---|
| Pre-Exercise | Negative | 16 | 17 | 17 | 17 |
| Post-Exercise | Negative | 16 | 13 | 10 | 13 |
|  | Trace | 0 | 3 | 5 | 3 |
| 60 | Negative | 9 | 8 | 10 | 8 |
|  | Trace | 6 | 5 | 5 | 5 |
|  | 30-100+ | 1 | 2 | 0 | 3 |
|  | 100+ |  | 1 | 1 |  |
| 90 | Negative | 10 | 12 | 11 | 9 |
|  | Trace | 4 | 4 | 0 | 5 |
|  | 30-100 | 1 | 1 | 0 | 2 |
|  | 100+ |  |  | 1 |  |
| 120 | Negative | 16 | 16 | 11 | 13 |
|  | Trace | 0 | 1 | 1 | 4 |
|  | 30-100 |  |  | 1 |  |
| 180 | Negative | 15 | 16 | 10 | 13 |
|  | Trace | 0 | 0 | 1 | 2 |
| 240 | Negative | 15 | 16 | 10 | 11 |
|  | Trace | 0 | 0 | 1 | 5 |

In regards to sensory acceptability, the differences between G30 and G18 were few and rather random. Although the G30 formula was initially less acceptable than the G18 for overall acceptance, flavor, sweetness, and tartness at the initial sensory read (32 minutes into recovery time), the differences between these two beverages decreased rapidly with time. While G18 generally had a numerical score advantage at 42, 62, and 82 minutes in these categories, the advantage was statistically insignificant. The G30 formula scored lower than the G18 for tartness at 62 minutes.

W scored lower than G18 for overall acceptance and flavor at all evaluation times. It also scored lower for aftertaste than G18 at the initial evaluation (32 minutes).

The G18 formula was rated less salty than ideal at all evaluation times. G18 was rated more sour than ideal at 32, 42, and 82 minutes. There were no differences in perceived saltiness between G18 and G30. Compared to G18, G30 was less sour at 42 and 62 minutes, sweeter at 82 minutes, and less off at 62 minutes. The G30 formula was rated less salty than ideal at all evaluation times.

EXAMPLE 6

This study compared the electrolyte formulations shown below to determine how rapidly fluid is lost and how much is retained up to three hours after exercise-induced dehydration that is followed by replacement of total fluid loss from sweat.

| CODE | [Na], mEq/L | [K], mEq/L | [Cl], mEq/L | Osmolality, mOsm/kg |
|---|---|---|---|---|
| G18 | 18.4 | 2.8 | 11.5 | 307 |
| G25 | 25.1 | 9.7 | 33.9 | 339 |
| G30 | 29.7 | 2.7 | 20.2 | 325 |

In addition, the study was to determine the effects of lowering the sodium to 25 mEq/L while increasing the sum of the total extracellular ions—sodium and chloride—to levels above the G30 formulation.

For this study, subjects were divided into two groups to assess the effect of controlling pre-experiment diet (over 24 hours) on physiology measures. As in the previous phase, subjects were fed a standard diet for dinner the evening prior to testing, and for breakfast and lunch the day of the test.

For the controlled dietary group the total caloric intake was 2200 calories and approximately 2400 mg of sodium. Subjects who weighed over 150 pounds had slightly higher (+200) calories and sodium intake (+100 mg). All subjects were given a written copy of the dietary and exercise guidelines, and subjects were instructed not to substitute foods, but additional liquids (within guidelines) were permitted until 3 hours prior to the experiment.

All subjects were required to follow the diet and exercise guidelines prior to participating. In order to assure pre-experiment hydration, each subject was required to ingest adequate fluid. Pre-experiment hydration was further assured by checking the conductivity of the pre-experiment urine sample collected immediately prior to the testing. Subjects whose first experimental urine sample had a conductivity that exceeded 21 millisiemens-cm were dismissed from the experiment and required to reschedule.

Thirty-six subjects (31 men, 5 women) completed the study. On separate occasions, they exercised in the heat (80° F./40% RH) for 1.5 hours and dehydrated on average 1.8±0.6% and replaced 100% of their sweat loss with one of three levels of sodium (18, 25, or 30 mEq/L). Average sweat rate for the entire group across all trials was 0.885±0.32 liters per hour.

Figure 21:
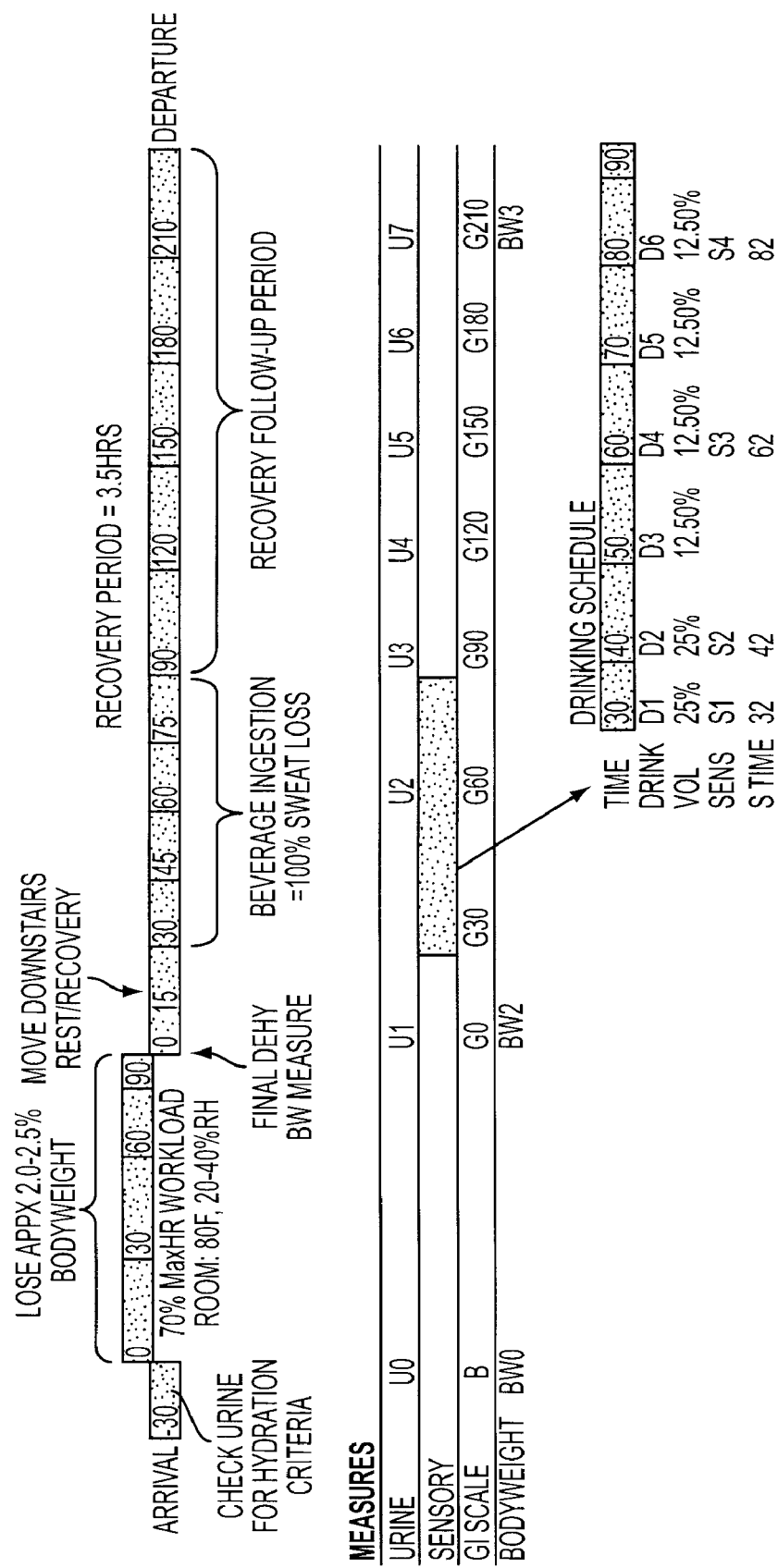
FIG. 21 illustrates the experimental protocol used to determine how much fluid is retained up to three hours after exercise-induced dehydration that is followed by replacement of total sweat loss.

Women were included in this study and the effects associated with changes in the menstrual cycle, fluid balance, and hormonal influence were controlled by studying the women when they were in the same phase of their cycle for all testing. This study was designed to determine the rate of fluid loss after ingesting beverages with varying mineral content following exercise-induced dehydration in the heat. The testing protocol and sequence are shown in FIG. 21.

Subjects were then weighed for a baseline bodyweight, and a sensory (GI Symptoms, Energy levels) questionnaire was completed. Subjects cycled in a warm environment (80° F., 40% RH) for 1.5 hours to elicit an exercise-induced dehydration near two percent of initial bodyweight. A previously determined workload was used to set an exercise intensity equivalent to 70-75% of maximal heart rate as determined by earlier maximal treadmill tests. Heart rate was monitored every 10 minutes using a telemetered HR monitor (Polar) and to assure sufficient intensity of exercise.

At 1-hour, subjects were allowed a 5-minute break from cycling. At the end of the exercise-dehydration period, subjects were given a sensory form, and subjects were weighed again to determine final sweat loss. A post-exercise urine sample was collected immediately following the post-exercise body weight. The subjects were then seated in a reclined position for the remainder of the recovery period.

Beverages were mixed prior to the experiment using 1-liter and 2-liter volumetric flasks and beverage grade water that did not contribute any electrolytes to the beverage. Beverages were served chilled from the refrigerator (approximately 40° F.), although the last two beverages were likely to be closer to ambient temperature by the time they were served to the subjects. Beverages were distributed according to a rehydration scheme that involved dosing the volume according to specific times. At 30 minutes into recovery, subjects received their first of six cups of beverage, followed by another cup every ten minutes. Total beverage volume was equivalent to total sweat loss, and was portioned such that subjects received 50% of the total volume in the first 20 minutes and the remaining 50% in 12.5% portions every ten minutes for the remaining 40 minutes. All fluid was consumed within an hour.

Every 30 minutes during the 3.5-hour recovery, subjects were given a sensory form to complete, and urine samples were taken. Urine volume was determined by weight, and urine conductivity was immediately determined using a conductivity meter (WTW LF 340, model 19706-20). Urine was then aliquoted and stored at −20° F. until later analysis for [Na+] and [K+]. Urine [Na+] and [K+] were determined using flame photometry (IL943 Automatic Flame Photometer) after centrifuging for 15 minutes to remove any insoluble particles from the sample to be analyzed.

Data were analyzed using a computer statistics package (SPSS, v.10). Descriptive statistics and summary tables were generated for all dependent measures. Repeated measures ANOVA was used to test for main effects of treatment and where appropriate time dependent effects. Where main effects existed, a Duncan post-hoc test was used to determine statistical differences among means. Comparisons were tested with an alpha level equal to 0.05. Effect size estimates were made for comparisons of total urine loss between treatments.

Study results are broken into separate groups. Results for the entire study group are shown first, followed by diet-controlled men, then by men only.

Thirty-six subjects (N=36) completed all three trials. Four subjects either withdrew or were dismissed from the study due to illness, or inability to tolerate dietary restriction (caffeine withdrawal). Average loss of bodyweight during the exercise-induced dehydration was 1.8±0.6% over 1.5 hours. The subjects exhibited an average sweat rate of 0.89±0.32 liters/hr and lost an average of 1.3±0.5 liters of sweat during the dehydration period. Dehydration and sweat loss did not differ across treatments.

The percent of ingested fluid retained differed significantly. G25 resulted in significantly more fluid retention (79.6%) compared to G18 (73.5%) and G30 (75.1%). When corrected for bodyweight (ml/kg) or examined in absolute terms (kilograms), the significant effect disappears. Contrary to results from Project FR-1 phases 2, 3, and 4, G30 did not differentiate from G18 in this study. Estimates of effect size (ES) for percent fluid retained are as follows: 18 vs. 25, ES=0.55 (medium effect size); 18 vs. 30, ES=0.15 (no effect); 25 vs. 30, ES=0.47 (medium effect size).

Average total urine excreted during 2.5 hours of recovery was significantly less with G25 (0.252 L) than with G30 (0.322 L) and G18 (0.349 L). When corrected for bodyweight (e.g. ml/kg) the effect holds significant. Effect size estimates were made for the following comparisons for total urine loss: 18 vs. 25, ES=0.57 (medium effect size, significant); 18 vs. 30, ES=0.14 (no effect); 25 vs. 30, ES=0.49 (medium effect size, non-significant). Formulations began to differentiate at 150 minutes of recovery (1 hr after drinking was complete).

Absolute change in body weight from baseline to end of recovery was −0.72, −0.62, and −0.71 kilograms for G18, G25, and G30, respectively. Expressed as a percentage of initial weight, these values were −0.98%, −0.84%, and −0.96% for G18, G25, and G30, respectively. Both absolute and percentage variables were significantly different for G25 versus G18 and G30 when subject variability was controlled for in the statistical model. G18 did not differ from G30.

Mean Specific Electrical Conductivity (SEC) for baseline urine samples ranged between 17-18 mS-cm across all treatments. Average baseline urine volumes were 111.4, 117.1, and 121.8 grams for G18, G25, and G30 respectively. On average, this indicates that subjects started the protocol in moderately hydrated state.

Average urine volumes excreted, independent of time, were 58.2, 42.0, and 53.7 grams, for G18, G25, and G30, respectively. Interestingly, mean SEC independent of time was 13.1, 16, and 14.5 mS-cm for G18, G25, and G30, respectively.

To examine any sensory (taste) and perceptual changes associated with the various treatments, the subjects rated a number of psychophysiological characteristics on several different scales (e.g. categorical, 100 pt) throughout the experimental period. Both a GI distress and a Sensory (taste) form were used periodically throughout the test to examine subjects feelings.

There were no differences across products for any ratings on the GI form. This included aspects of: energy, alertness, thirst, hunger, stomach fullness, nausea, and urge to urinate.

Some sensory attributes of the different products were rated significantly different. Overall acceptance across products showed similar scores when the beverages were first received, but differed significantly at the last beverage (82 min). G25 had significantly less appeal (6.4) compared to G18 (7.0), but did not differ from G30 (6.8). Liking of saltiness was less for G25 compared to G18 and G30 for all time points tested. This may indicate a negative attribute of the additional chloride in G25. While not significant, G25 was perceived directionally more salty than G18 or G30. Liking of flavor scores were similar across time and product. GI attributes varied over time, consistent with the time of day and protocol. There were no remarkable differences to report. Taste and flavor attributes of the different products did not vary over the short duration (1-hr) that they were consumed.

Further probing of the data was completed with subgroups as defined below. This was done in response to learning that a variety of factors had significant impact on the outcome. The following results are from analyses in subgroups of: Diet Controlled (Men Only); Men Only. Due to the few women participants, it worked out such that there were only men in the group that tested with a controlled diet.

Seventeen (n=17) of the 36 subjects were stratified into the group of men that ate a controlled diet. In this subset of participants, average loss of bodyweight during the exercise-induced dehydration was 1.8±0.5% over 1.5 hours. These subjects exhibited an average sweat rate of 0.95±0.28 liters/hr and lost an average of 1.4±0.4 liters of sweat during the dehydration period. Dehydration and sweat loss did not differ across treatments.

The percent of ingested fluid retained in this subgroup did not differ significantly (p=0.089). Directionally, G25 resulted in significantly more fluid retention (80.7%) compared to G18 (74.9%) and G30 (74.2%), but the differences were not great enough for this subset to reach statistical significance.

Total urine loss varied by sodium level (p=0.029). Average total urine excreted during 2.5 hours of recovery was significantly less with G25 (0.255 L) than with G30 (0.374 L) and G18 (0.367 L). Effect sizes are as follows: 18 vs. 25, ES=0.58 (medium effect size); 18 vs. 30, ES=0.04 (no effect); 25 vs. 30, ES=0.71 (large effect size).

Absolute change in body weight from baseline to end of recovery was −0.70, −0.59, and −0.75 kilograms for G18, G25, and G30, respectively (p=0.015). Expressed as a percentage of initial weight, these values were −0.94%, −0.79%, and −0.99% for G18, G25, and G30, respectively. Both absolute and percentage variables were significantly different for G25 versus G18 and G30 when subject variability was controlled for in the statistical model. G18 did not differ from G30.

Thirty-one (n=31) of the 36 subjects were stratified into a group of men, independent of diet control group. In this subset of the entire group, the largest differences were noted, perhaps due to the large sample size (n=31) and statistical removal of the effect imposed by the small group of women tested. In this subset of participants, average loss of bodyweight during the exercise-induced dehydration was 1.9±0.6% over 1.5 hours. These subjects exhibited an average sweat rate of 0.94±0.31 liters/hr and lost an average of 1.4±0.5 liters of sweat during the dehydration period. Dehydration and sweat loss did not differ across treatments.

Figure 22:
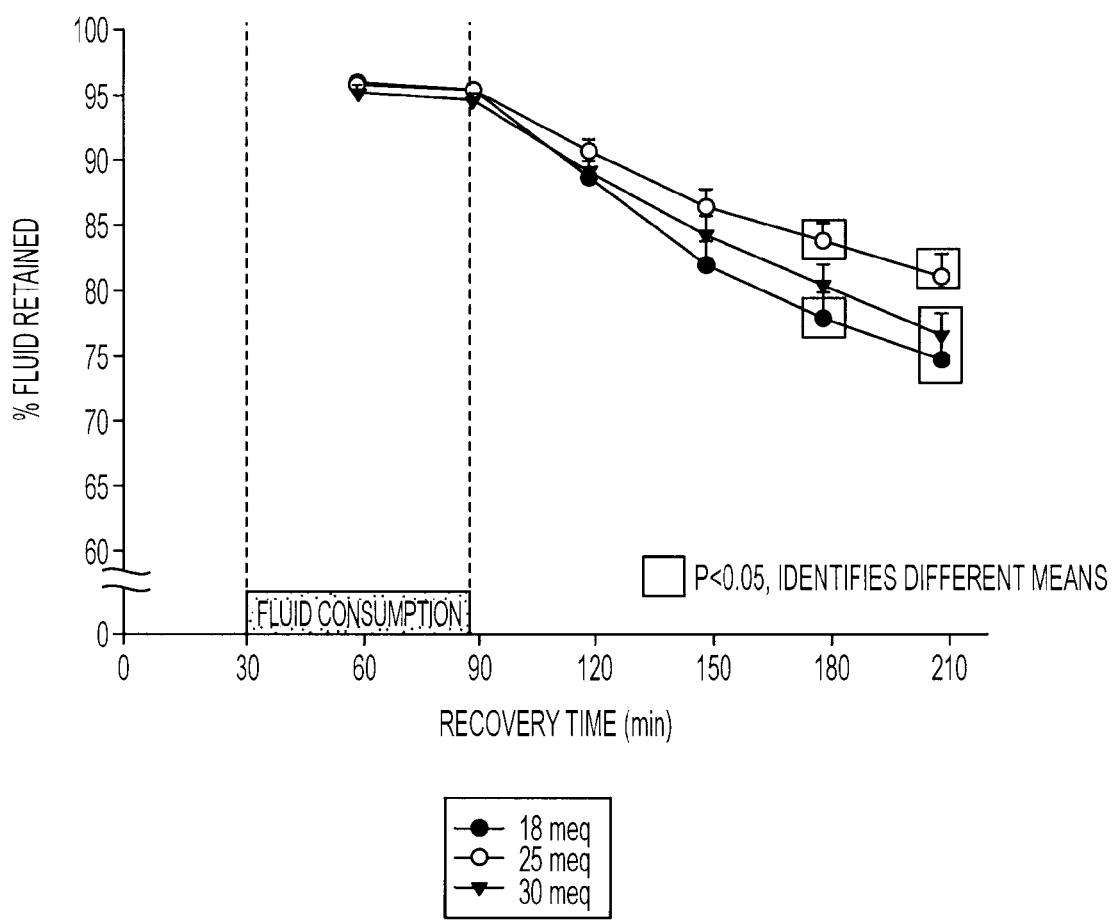
FIG. 22 shows the percentage of fluid retained over time of the various formulations.

The percent of ingested fluid retained differed significantly (p=0.016). G25 resulted in significantly more fluid retention (79.6%) compared to G18 (73.1%) and G30 (75.0%). The treatment effects became apparent at 150 minutes into the recovery segment [see FIG. 22]. When corrected for body-weight (ml/kg) or examined in absolute terms (kilograms), the significant effect disappears.

Figure 23:
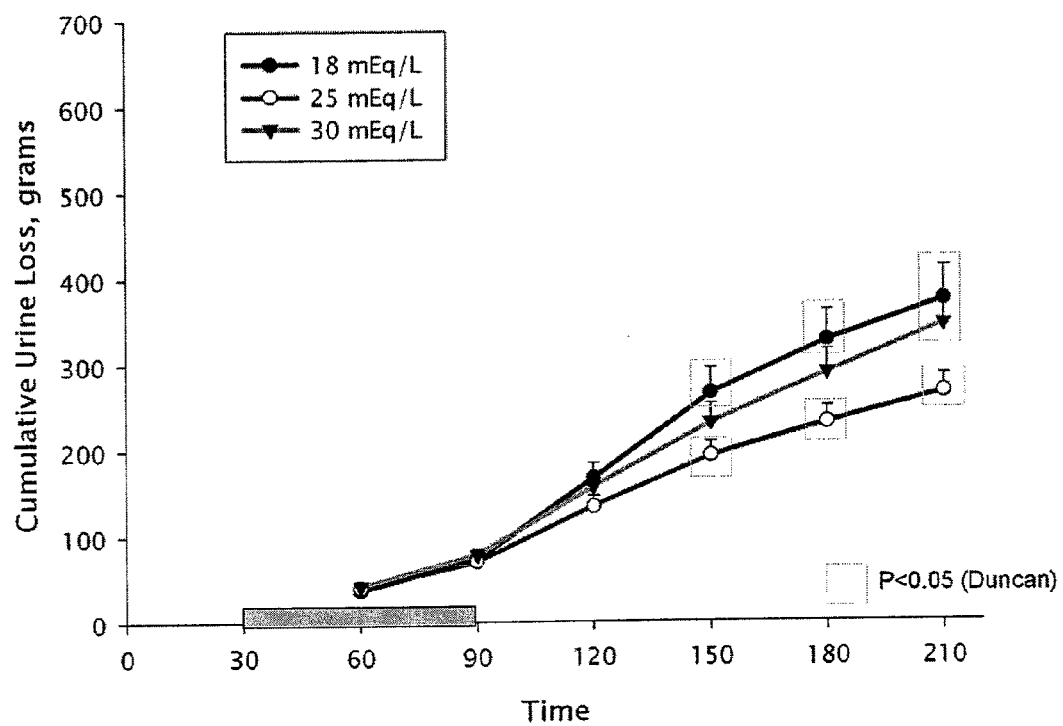
FIG. 23 shows the cumulative urine loss in grams over time of the various formulations.

Average total urine excreted during 2.5 hours of recovery was significantly (p=0.009) less with G25 (0.267 L) than with G30 (0.346 L) and G18 (0.374 L). When corrected for body-weight (e.g. ml/kg) the effect holds significant (p=0.005). Products began to differentiate at 150 minutes of recovery (1 hr after drinking was complete) [see FIG. 23]. Effect size estimates are as follows: 18 vs. 25, ES=0.62 (medium effect size); 18 vs. 30, ES=0.15 (no effect); 25 vs. 30, ES=0.56 (medium effect size).

Absolute change in body weight from baseline to end of recovery was −0.76, −0.65, and −0.75 kilograms for G18, G25, and G30, respectively. Expressed as a percentage of initial weight, these values were −1.01%, −0.85%, and −0.99% for G18, G25, and G30, respectively. Both absolute (p=0.006) and percentage variables (p=0.010) were significantly different for G25 versus G18 and G30 when subject variability was controlled for in the statistical model. G18 did not differ from G30.

The data are consistent with findings reported for the entire group. There are sporadic differences between beverages. The most notable effect observed was that 'liking of saltiness' was lowest and perceived saltiness was highest for G25 compared to G18. This effect was fairly consistent throughout the entire drinking period. There were no remarkable GI related effects observed across the beverages in this subgroup of men.

EXAMPLE 7

This study was similar to the previous one. This time however, the sum of chloride and sodium ions in 25 mEq/L formulation was more similar to the sum of sodium and chloride in the G30 formulation and the 18 mEq/L formulation was not included. Specific formulations of the electrolytes are shown below.

| Code | $[Na^+]$, mEq/L* | $[K^+]$, mEq/L* | $[Cl^-]$, mEq/L | $[Mg^{++}]$, mEq/L | Osm (mOsm/kg)* |
|---|---|---|---|---|---|
| G25 | 25.1 | 9.9 | 30 | 2 | 339 |
| G30 | 29.5 | 2.8 | 20 | 0 | 334 |

These formulations were compared for their effects on fluid loss and fluid retention. In addition, their sensory qualities were measured.

Subjects reported to the laboratory and workloads were set for the bicycle and treadmill sufficient to produce intensities between 75-80% of their measured maximum heart rates (determined from annual stress tests). In addition, body weights were obtained prior to and following the orientation exercise session in order to predict sweat rates.

Subjects were provided with standardized meals to ensure consistent sodium intake (~2700 mg) prior to each of the two trials. Meals included dinner (evening prior to testing), and breakfast and lunch on the day of testing. Subjects were given the option of eating all or a portion of the food provided but were instructed to record which foods and amount left uneaten. These items were then withheld from the food bags for the next trial. In addition, they were given bottled water to drink the evening before and during the testing day to ensure adequate hydration. Subjects were asked to refrain from caffeine and alcohol use for 24-hours prior to the experiment.

Subjects included trained men (ages 25-49). Seventeen completed both trials. One subject withdrew from testing due to illness. Subjects reported to the facility following a 3-hour fast (drinking and eating), a urine sample was taken to assess pre-exercise hydration status and were weighed.

After completing a pre-exercise survey (GI ratings), they began exercise. The exercise session consisted of alternate cycling/running at 15-minute intervals at 75-80% maximum heart rate for a total of 60 minutes. Heart rates were taken at 15-minute intervals to ensure subjects maintained adequate intensity. Subjects refrained from drinking during the entire exercise period in an effort to produce 1.5-2% dehydration.

Following exercise, subjects were weighed and a post-exercise urine sample was taken. A 3.5 hour recovery period followed. At 30 minutes into recovery, subjects were given their first beverage equivalent to 25% of their total sweat loss (determined by subtracting post-exercise weight from pre-exercise weight) and a sensory questionnaire. A questionnaire and beverage (25% of losses) was given again at 40 minutes into recovery. Drink #3, equivalent to 12.5% of sweat loss, was given at 50 minutes. At 58 minutes, subjects were given a GI scale to assess gastrointestinal responses and were escorted to the restroom for a urine sample. They filled out a sensory form when they returned and were given their $4^{th}$ drink (12.5%). Drink #5 (12.5%) was given at 70 minutes, drink #6 (12.5%), their final drink, and a sensory questionnaire was given at 80 minutes. At 90, 120, 180 and 240 minutes, GI scales were given and urine samples were collected. After the final urine sample, subjects were taken back upstairs for a final nude body weight. They were given meals for the next trial (if necessary) and were released.

Urine volume was determined by weight and urine specific gravity was measured (A 300 Clinical Refractometer). Urine was the transferred into 4-ml cryovials for further analysis. Urine [Na+] and [K+] were determined using flame photometry (IL943 Automatic Flame Photometer) after centrifuging for 15 minutes to remove any insoluble particles from the sample to be analyzed. Osmolality was measured for each sample (Fiske 2400 Osmometer).

Each subject was given food equaling 2,428 kcal and 2,694 mg of sodium. They were instructed to eat as much or as little as they desired, but to remain consistent between treatments. Most subjects ate all the food provided to them, however, intakes ranged from 1,851-2,428 kcal and 1,831-2694 mg sodium. None of the subjects ate food other than what was provided.

The 60-minute exercise session resulted in similar levels of dehydration between treatments (1.75±0.29% and 1.78±0.33% for G25 and G30, respectively). In addition, sweat rates between treatments were essentially the same (1.39±0.32 L/hour for G25 and 1.40±0.32 L/hour for G30).

Total fluid intake between treatments was 1.39±0.32 L for the G25 treatment and 1.40±0.32 L for the G30 treatment matching the values for total sweat losses.

Total cumulative fluid output was not different between treatments (0.35±0.13 L G25, 0.35±0.15 L G30). Additionally, urine output at each data collection point was not significantly different between treatments (See below).

| Treatment | 60 minutes | 90 minutes | 120 minutes | 180 minutes | 240 minutes |
|---|---|---|---|---|---|
| G25 | 35.28 ± 19.65 | 73.39 ± 25.04 | 159.68 ± 59.36 | 276.23 ± 104.25 | 345.80 ± 130.13 |
| G30 | 37.55 ± 22.40 | 70.58 ± 37.21 | 153.47 ± 86.35 | 272.45 ± 138.93 | 352.41 ± 152.08 |

Each time point represents the number or minutes into recovery.

Fluid retention, or the amount of fluid consumed that was not excreted as urine, was not different between treatments. This was calculated in both relative terms (ml/kg) and as a percentage calculated as (fluid in-fluid out)/fluid in. Relative fluid retention was 13.11±3.04 ml/kg and 13.32±3.52 ml/kg for G25 and G30, respectively. Percent fluid retained was also the same for both treatments (74.29±9.76% for G25 and 74.20±10.14% for G30). Predictably, percent fluid retention across time was also the same for each treatment (see below).

| Treatment | 60 minutes | 90 minutes | 120 minutes | 180 minutes | 240 minutes |
|---|---|---|---|---|---|
| G25 | 95.86 ± 2.10 | 94.54 ± 1.69 | 88.00 ± 5.03 | 87.74 ± 8.84 | 74.29 ± 9.76 |
| G30 | 95.31 ± 3.44 | 94.56 ± 3.22 | 88.25 ± 7.45 | 89.02 ± 10.50 | 74.20 ± 10.14 |

Figure 24:
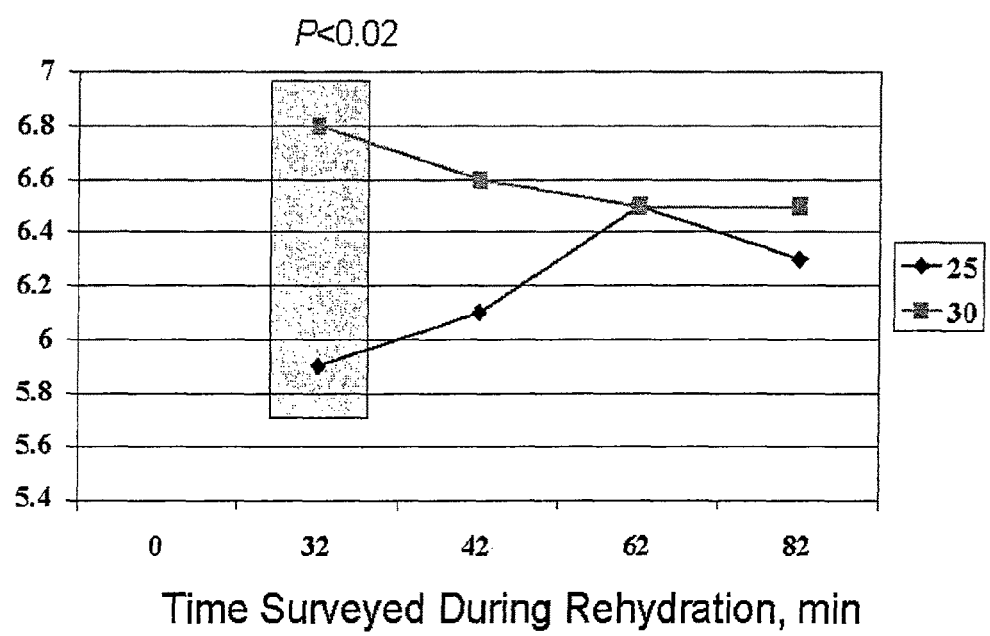
FIG. 24 indicates the overall acceptance of the various formulations during the rehydration period preceding the measurement of fluid retention.
Figure 25:
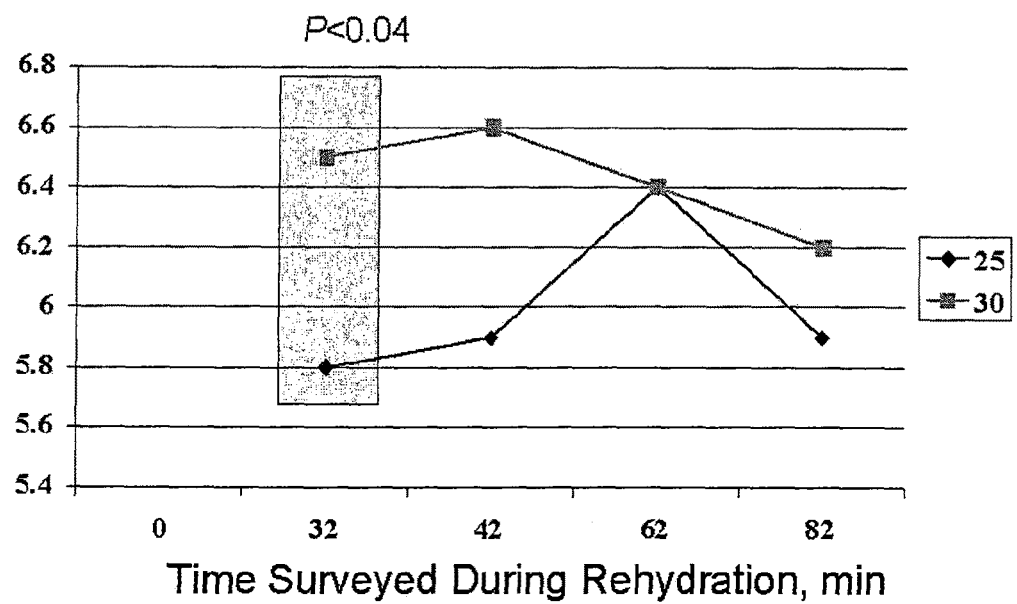
FIG. 25 indicates the tartness scores of the various formulations during the rehydration period preceding the measurement of fluid retention.
Figure 26:
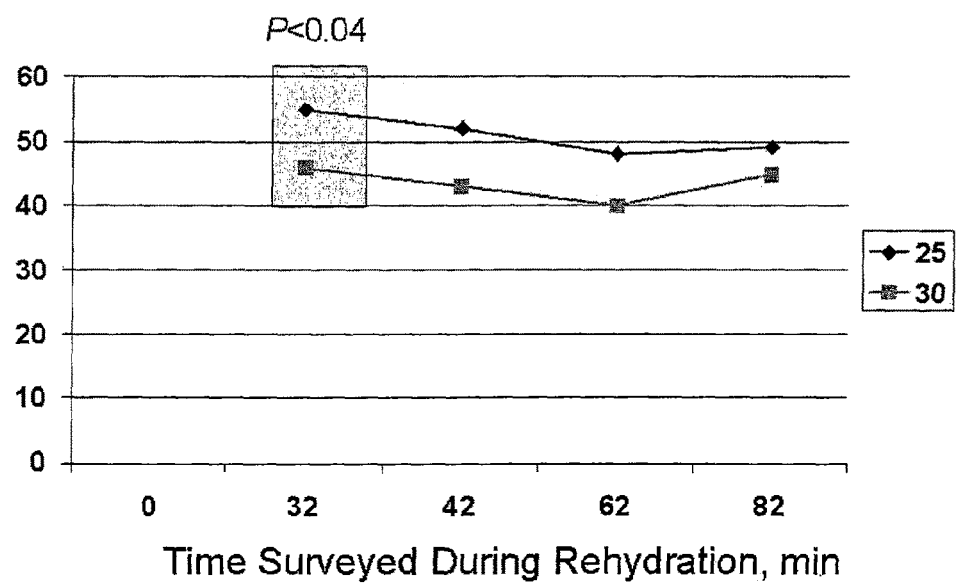
FIG. 26 indicates the perceived saltiness of the various formulations during the rehydration period preceding the measurement of fluid retention.

Subjects were asked to rate a number of psychophysiological characteristics on several different scales (e.g. categorical, 100 pt) throughout the experiment period to examine any sensory and perceptual changes associated with the treatments. A GI distress and a Sensory (taste) form were used periodically throughout the test to examine subjects' perceptions. There were no important differences between the two beverages on ratings of perceived physiological and psychological well-being. Differences in beverage acceptance are as follows. The G30 scored significantly higher than G25 in acceptance and liking of sweetness, tartness, flavor, and saltiness, and had a large effect size (0.7) advantage in aftertaste at 32 minutes. See FIG. 24 for overall acceptance. At 42 minutes, G30 was significantly more acceptable than G25 for aftertaste, and had a medium effects size advantage in tartness. G25 was more tart than G30 at all times. See FIG. 25. G25 was significantly more salty than G30 at 32 minutes and was not different at all other time points. G25 perception of saltiness was initially rated as ideal but became decreasingly less than ideal at all other time points. G30 was less than ideal saltiness at all time points. See FIG. 26.

EXAMPLE 8

This study determined the effects on rehydration of modifying the G30 formula to include calcium and magnesium and a higher level of potassium. As in Example 5, the G18 and POWERade® formulations were included along with two modified versions of G30 labeled K10 and K20. As in all Examples, subjects as well as the experimenters were blinded to the beverage treatments. Specific formulations of the electrolytes are shown below.

| Code | [Na], mEq/L | [K], mEq/L | [Cl], mEq/L | [Ca], mEq/L | [Mg], mEq/L |
|---|---|---|---|---|---|
| P | 5 | 3 | ~6 | 0 | 0 |
| G18 | 18 | 3 | ~12 | 0 | 0 |
| K10 | 30 | 10 | ~20 | 1 | 3 |
| K20 | 30 | 20 | ~20 | 1 | ~6 |

Subjects were provided with standardized meals to ensure consistent sodium intake (~3000 mg) prior to each of the experimental trials. Meals included dinner (evening prior to experiment), and breakfast and lunch on the day of testing. Subjects were given the option of eating all or a portion of the food provided. They were also instructed to record which foods were left uneaten. These items were then withheld from the food bags for the next trial. In addition, they were given bottled water to drink the evening before (500 ml) and during the testing day (1000 ml) to ensure adequate hydration. Subjects were asked to refrain from caffeine and alcohol use for 24-hours prior to the experiment.

Subjects included trained men ages 30-50 y. Seventeen completed both trials. Testing followed a 3-hour fast (drinking and eating). Body weights were obtained prior to and following the exercise session. In addition, urine samples were taken to assess pre-exercise hydration status. Subjects also completed a pre-exercise survey (GI ratings).

The exercise session consisted of 30-minutes each on the cross trainer, stationary bike and treadmill at 70-75% maximum heart rate for a total of 90 minutes. Heart rates were taken at 15-minute intervals to ensure subjects maintained adequate intensity. Subjects refrained from drinking during the entire exercise period in an effort to produce 2-2.5% dehydration.

Following exercise, subjects were weighed and gave a post-exercise urine sample, followed by a 3.5 hour recovery period. Thirty minutes into recovery, subjects were given their first beverage equivalent to 25% of their total sweat loss (determined by subtracting post-exercise weight from pre-exercise weight) and a sensory questionnaire. A questionnaire and beverage (25% of losses) was given again at 40 minutes into recovery. The third aliquot of beverage, equivalent to 12.5% of sweat loss, was given at 50 minutes. At 58 minutes, subjects were given a GI scale to assess gastro-intestinal responses and urine samples were taken. Subjects then filled out a sensory form and were given their fourth aliquot (12.5%). The fifth aliquot (12.5%) was given at 70 minutes, and the sixth and final aliquot (12.5%) and a sensory questionnaire was given at 80 minutes. At 90, 120, 180 and 240 minutes, GI scales were given and urine samples were collected. After the final urine sample, subjects were weighed for a final nude body weight.

Urine volume was determined by weight and urine specific gravity was measured (A 300 Clinical Refractometer). Urine was then transferred into 4-ml cryovials for subsequent analysis of sodium and potassium concentrations using flame photometry (IL943 Automatic Flame Photometer) after centrifuging for 15 minutes to remove any insoluble particles from the sample to be analyzed. Osmolality was measured for each sample (Fiske 2400 Osmometer).

SPSS version 11.0 was used to analyze the data. ANOVA using a general linear model was used to determine differences between mean values. Data is reported as the mean±the standard deviation.

Exercise resulted in similar levels of dehydration between treatments (2.56±0.56%, 2.53±0.55%, 2.57±0.51%, and 2.50±0.44% for P, G18, K10, and K20, respectively). In addition, sweat rates between treatments were essentially the same (1.29±0.29 L/hr, 1.27±0.32 L/hr, 1.29±0.31, 1.26±0.26 L/hr P, G18, K10, and K20, respectively).

Total fluid intake between treatments was also similar between trials at 1.92±0.44 L for P, 1.92±0.48 L for G18, 1.93±0.46 L for K10 and 1.87±0.39 L for K20. The volume administered varied slightly in mean value because of the modest variability in sweat rate and the protocol of replacing 100% of the total sweat losses.

Final body weight as a percentage of initial body weight did not differ between treatments. Subjects returned to 98.68±0.53% of initial body weight following the P trial, 98.85±0.27% following G18, and 98.84±0.47% and 98.89±0.33% for K10 and K20, respectively.

Figure 32:
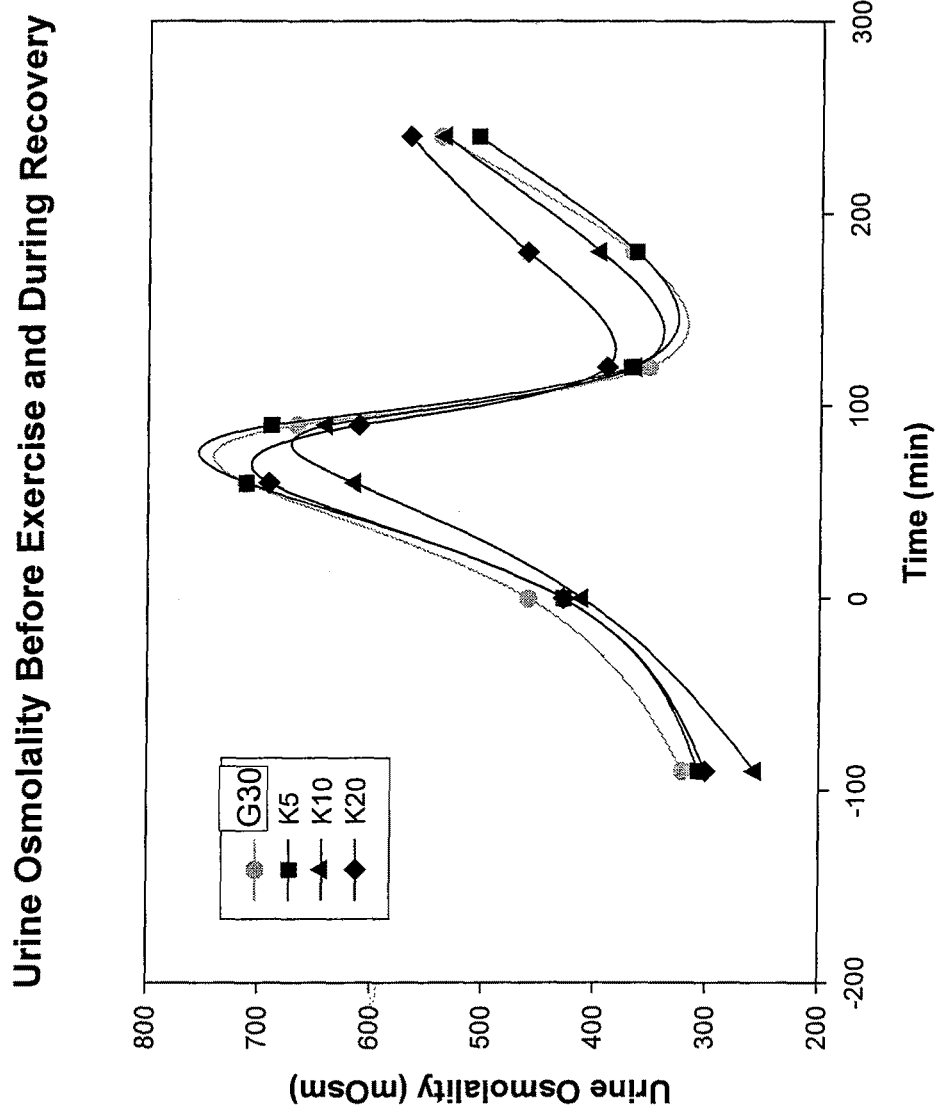
FIG. 32 shows the urine osmolality over time—before exercise and during recovery—for various formulations.

Total cumulative fluid output did not reach statistical significance between treatments (FIG. 32). Cumulative fluid output was 501.03±303.93 ml, 444.63±210.19 ml, 434.05±276.62 ml, and 353.08±183.47 ml, for P, G18, K10, and K20, respectively. Urine output at each data collection point was not significantly different between treatments for time points 60, 90 or 120. However, at time points 180 and 240, K20 resulted in significantly less urine loss than P.

Figure 27:
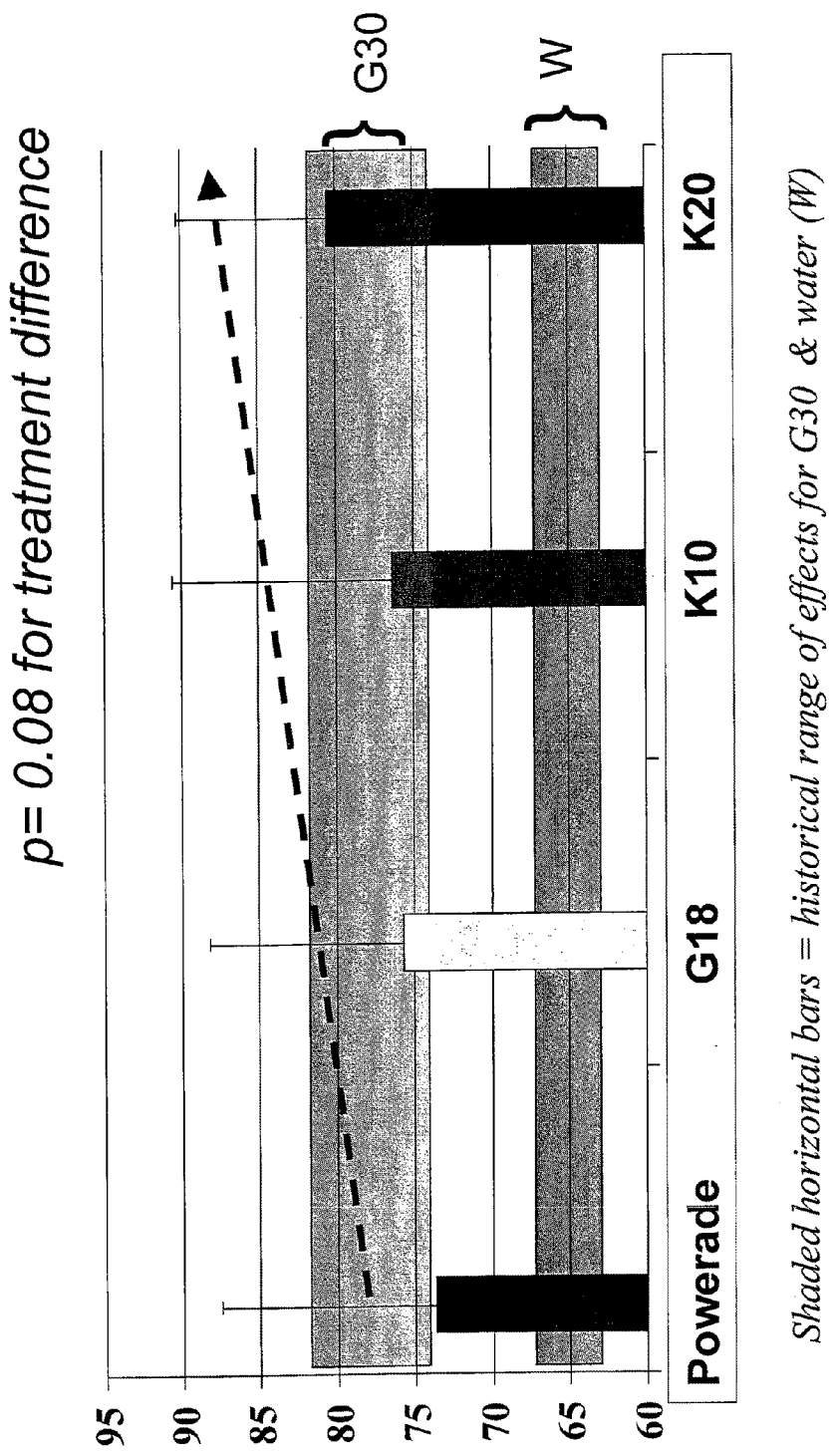
FIG. 27 shows the percent fluid retained as a percentage of the volume ingested during recovery time for various formulations and historical range of fluid retention.

Fluid retention, or the amount of fluid consumed that was not excreted as urine, was not different between treatments. This was calculated in both relative terms (ml/kg) and as a percentage calculated as (fluid in-fluid out)/fluid in. Relative fluid retention was 18.62±7.81 ml/kg, 19.40±5.65 ml/kg, 19.66±5.99 ml/kg, and 20.17±5.07 ml/kg for P, G18, K10 and K20, respectively. No statistical differences in percent fluid retained were found between treatments (73.70±13.85% for P, 75.74±12.56% for G18, 76.39±14.23% for K10, and 80.53±9.69% for G30). However, an effect size of 0.58 was found between K20 and P (p=0.09). See FIG. 27.

Total urine production during the recovery period was not significantly different between treatments. However, an effect size of 0.61 was found between the K20 treatment and P (p=0.07). Additionally, at time points 180 and 240 minutes, K20 was significantly different (less urine production) than P.

Figure 28:
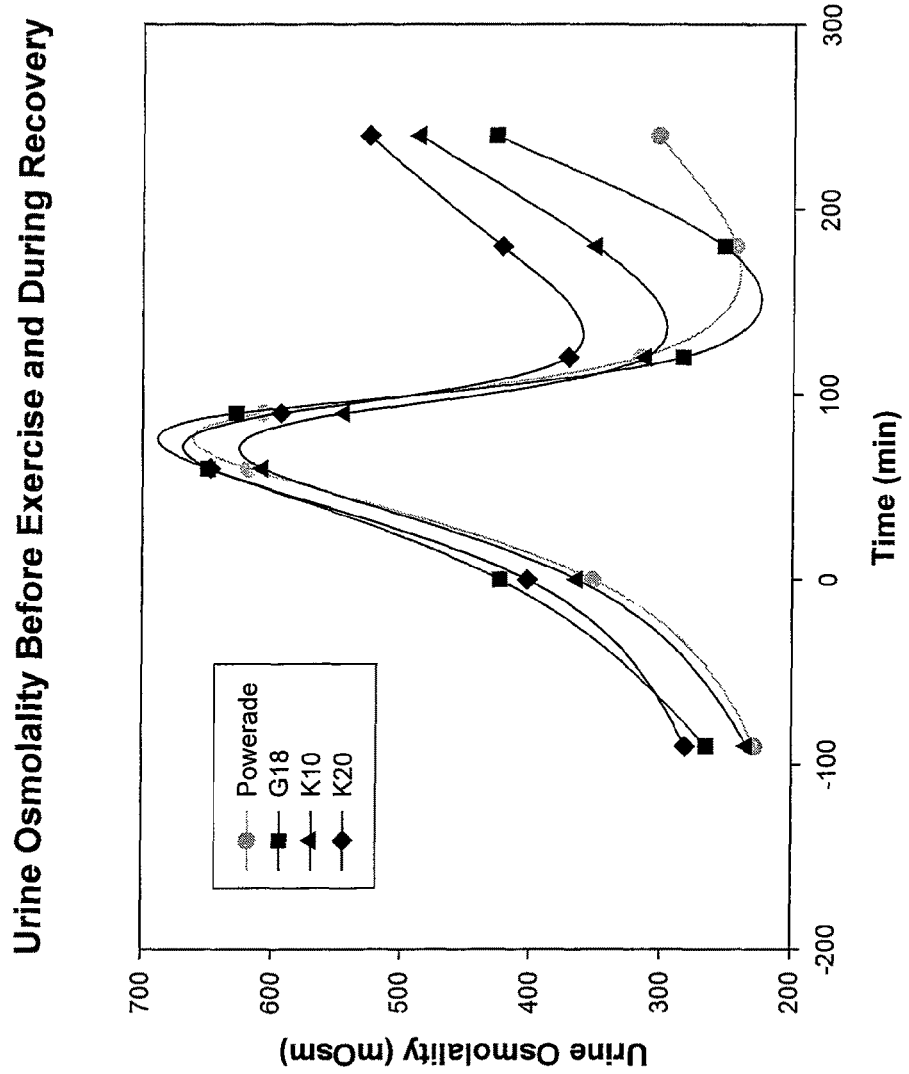
FIG. 28 shows the urine osmolality over time—before exercise and during recovery—for various formulations.

Mean urine osmolality was different between treatments. P resulted in the lowest urine osmolality (379.70±222.96 mOsm) and was not different than G18 (415.51±217.89 mOsm) or K10 (413.53±232.11 mOsm) but was significantly different than K20 (462.42±226.70 mOsm). K20 was not different than K10 or G18. See FIG. 28.

Figure 29:
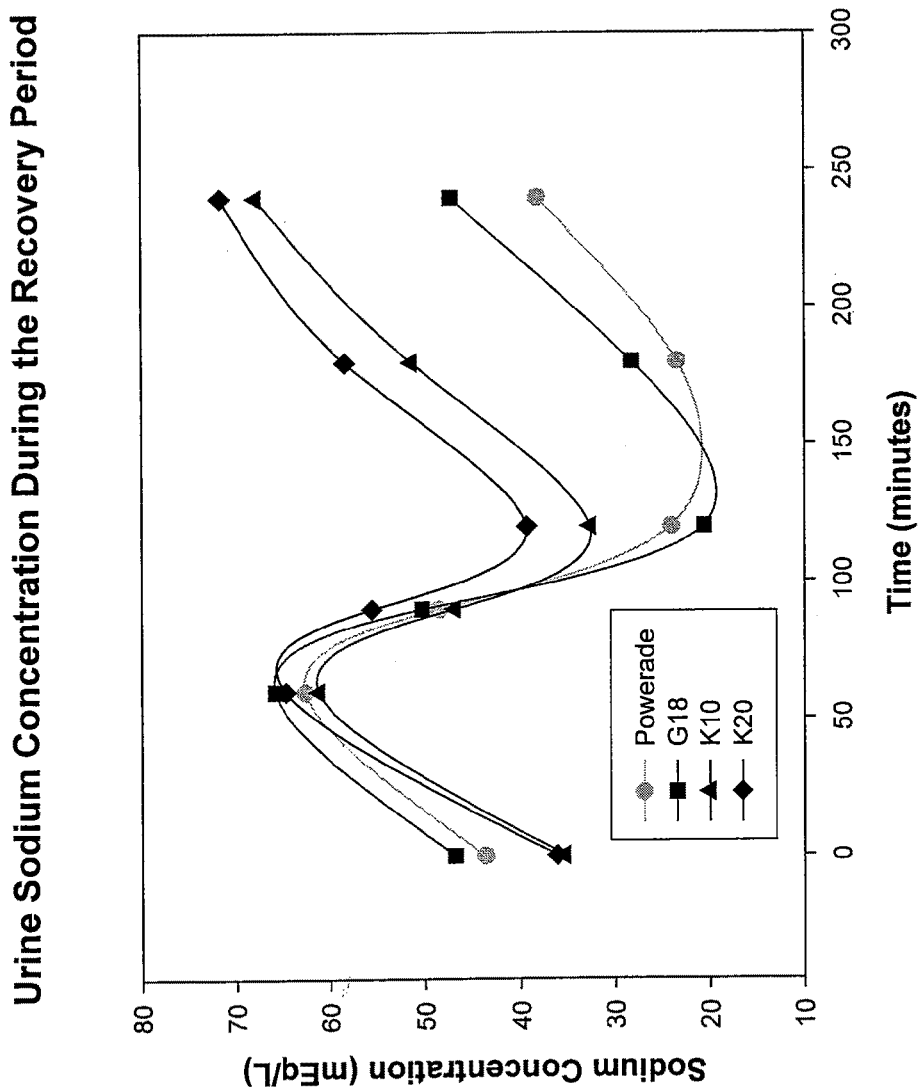
FIG. 29 shows the urine sodium concentration during the recovery period for various formulations.

Average urine sodium concentration was significantly greater for the K20 trial (52.59±31.38 mEq/L) compared to P (40.74±28.58 mEq/L) and G18 (43.81±27.98 mEq/L). K10 (47.87±35.18 mEq/L) was not significantly different than any of the trials. Total sodium excretion (urine volume×urine sodium concentration) was not different across trials (P=16.62±8.32; G18=17.68±10.80; K10=19.46±10.17; K20=20.27±8.77). See FIG. 29.

The average urine potassium concentration was significantly higher for the K20 trial (58.44±32.59 mEq/L) compared to P (42.24±40.19 mEq/L). G18 (47.26±37.05) and K10 (51.99±39.33) were not different from any of the treatments.

Figure 30:
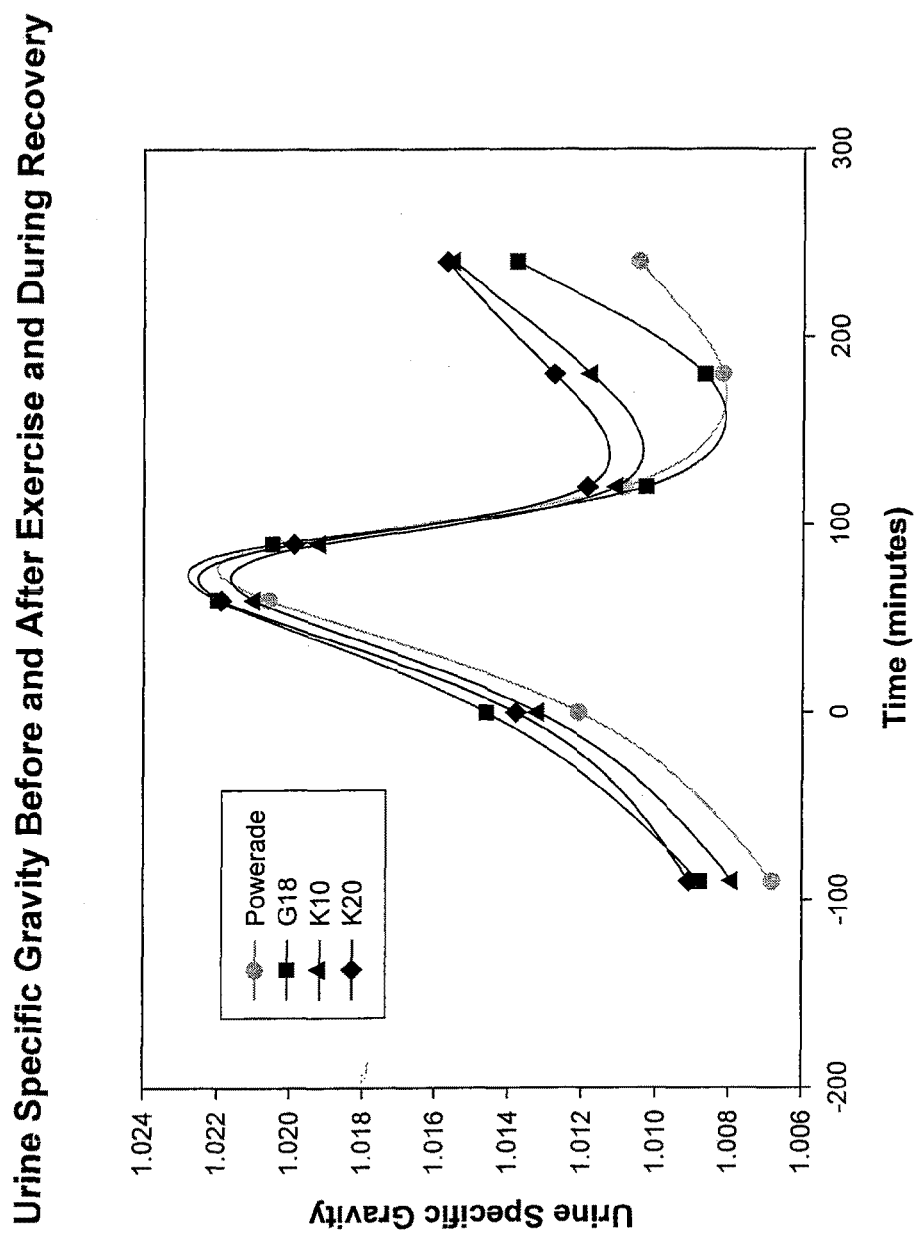
FIG. 30 shows the urine specific gravity over time—before and after exercise and during recovery—for various formulations.

Subjects began each exercise session well hydrated (USG=1.008±0.005). Urine specific gravity did not differ between treatments prior to exercise. Average USG for W treatment was significantly less than P at minute 120. Additionally W was less that G18 and G30 at minute 180. USG for P was significantly less than G30 at minutes 180 and 240. G18 and P were not different from each other at any time point. See FIG. 30.

There were no differences among the beverages for overall acceptance based on the sensory surveys taken at any of the four evaluation times. Formula K20 and Powerade scored significantly higher for saltiness acceptance than G18 at 32 minutes. This was the only case where a significant difference was found across products at any time. P showed a significant decline in overall acceptance with time. While P initially, had the numerically highest overall acceptance score, it was directionally the least acceptable overall. P also had directional decreases over time for all acceptance scales except aftertaste. Formula G18 had relatively low initial (32 minute) scores for liking of aftertaste, saltiness, and tartness. These scores rebounded into a more typical range at later times.

There were essentially no significant differences across the beverages for gastrointestinal distress. At 60 minutes, the K20 was rated as contributing to significantly more nausea than G18 and K10. This, however, was directionally consistent with the results at 30 minutes, since feelings of nausea are common following the exercise protocol and just before the beverages are administered. Numerous differences across time were observed. These were consistent with what would be expected from the protocol. No unusual states of gastric distress were observed.

EXAMPLE 9

Besides varying; the potassium levels and adding calcium and magnesium as done in the previous Example, the levels of all the electrolytes except for sodium were altered to determine their combined effects on rehydration. Three formulations were tested in addition to G30. All formulations consisted of 6% carbohydrate, 30 mEq/L of sodium and 0.103% flavoring. As in other Examples, the carbohydrate was a blend of sucrose (~3%), glucose (~1.7%) and fructose (~1.3%). Specific formulations of the electrolytes are shown below.

| Code | [Na], mEq/L | [K], mEq/L | [Cl], mEq/L | [Ca], mEq/L | [Mg], mEq/L |
|---|---|---|---|---|---|
| G30 | 30 | 3 | ~17 | 0 | 0 |
| K5 | 30 | 5 | ~20 | 3 | 3 |
| K10 | 30 | 10 | ~17 | 3 | 3 |
| K20 | 30 | 20 | ~17 | 1 | 3 |

The subjects included trained men (ages 19-50 y) Eighteen completed all four trials. Nearly identical to the previously examples, subjects were provided with standardized meals each day prior to the studies. Testing followed a 3-hour fast (drinking and eating). Prior to beginning exercise urine samples were obtained to assess pre-exercise hydration status and subjects were weighed.

The subjects exercised for a total of 90 minutes without consuming any fluids. The session consisted of 30-minutes each on the cross trainer, stationary bike and treadmill at 70-75% maximum heart rate for a total of 90 minutes. The exercise induced 2.5-3% dehydration in the subjects. After exercise, subjects were weighed and urine samples obtained, followed by a 3.5 hour recovery period.

Thirty minutes into recovery, subjects were given their first beverage equivalent to 25% of their total sweat loss (determined by subtracting post-exercise weight from pre-exercise weight) and a sensory questionnaire. A questionnaire and beverage (25% of losses) was given again at 40 minutes into recovery. The third aliquot of beverage, equivalent to 12.5% of sweat loss, was given at 50 minutes. At 58 minutes, subjects were given a GI scale to assess gastro-intestinal responses and sensation, and were escorted to the restroom for a urine sample. They then filled out a sensory form and were given a fourth aliquot (12.5%). The fifth aliquot (12.5%) was given at 70 minutes and the sixth and final aliquot (12.5%) and a sensory questionnaire was given at 80 minutes. At 90, 120, 180 and 240 minutes, subjects were again assessed for GI responses and had urine samples collected. After the final urine sample, subjects were weighed for a final nude body weight.

All urine samples were collected in disposable specimen containers, were weighed to determine the urine excretion volume and were measured for urine specific gravity (A 300 Clinical Refractometer). Urine was then transferred into 4-ml cryovials for subsequent analysis of sodium and potassium concentrations using flame photometry (IL943 Automatic Flame Photometer) after centrifuging for 15 minutes to remove any insoluble particles from the sample to be analyzed. Osmolality was measured for each sample (Fiske 2400 Osmometer).

Total sweat rates were lower than in past studies due to the difficulty in heating the room during the winter months. Nevertheless, sweat rates were sufficient to produce 2-2.5% dehydration. The exercise session resulted in similar levels of dehydration between treatments (2.10±0.50%, 2.18±0.51%, 2.14±0.53%, and 2.15±0.50% for G30, K5, K10 and K20, respectively). In addition, sweat losses between treatments were essentially the same (1.12±0.25 L/hr, 1.16±0.27 L/hr, 1.14±0.26, 1.14±0.25 L G30, K5, K10, and K20, respectively).

Total fluid intake between treatments was also similar between trials at 1.68±0.38 L for G30, 1.75±0.40 L for K5, 1.71±0.39 L for K10 and 1.72±0.37 L for K20. The volume administered varied slightly in mean value because of the modest variability in sweat rate and the protocol of replacing 100% of the total sweat losses.

Final body weight as a percentage of initial body weight did not differ between treatments. Subjects returned to 98.96±0.21% of initial body weight following the G30 trial, 98.96±0.29% following K5, and 98.90±0.37% and 98.95±0.31% for K10 and K20, respectively.

Figure 31:
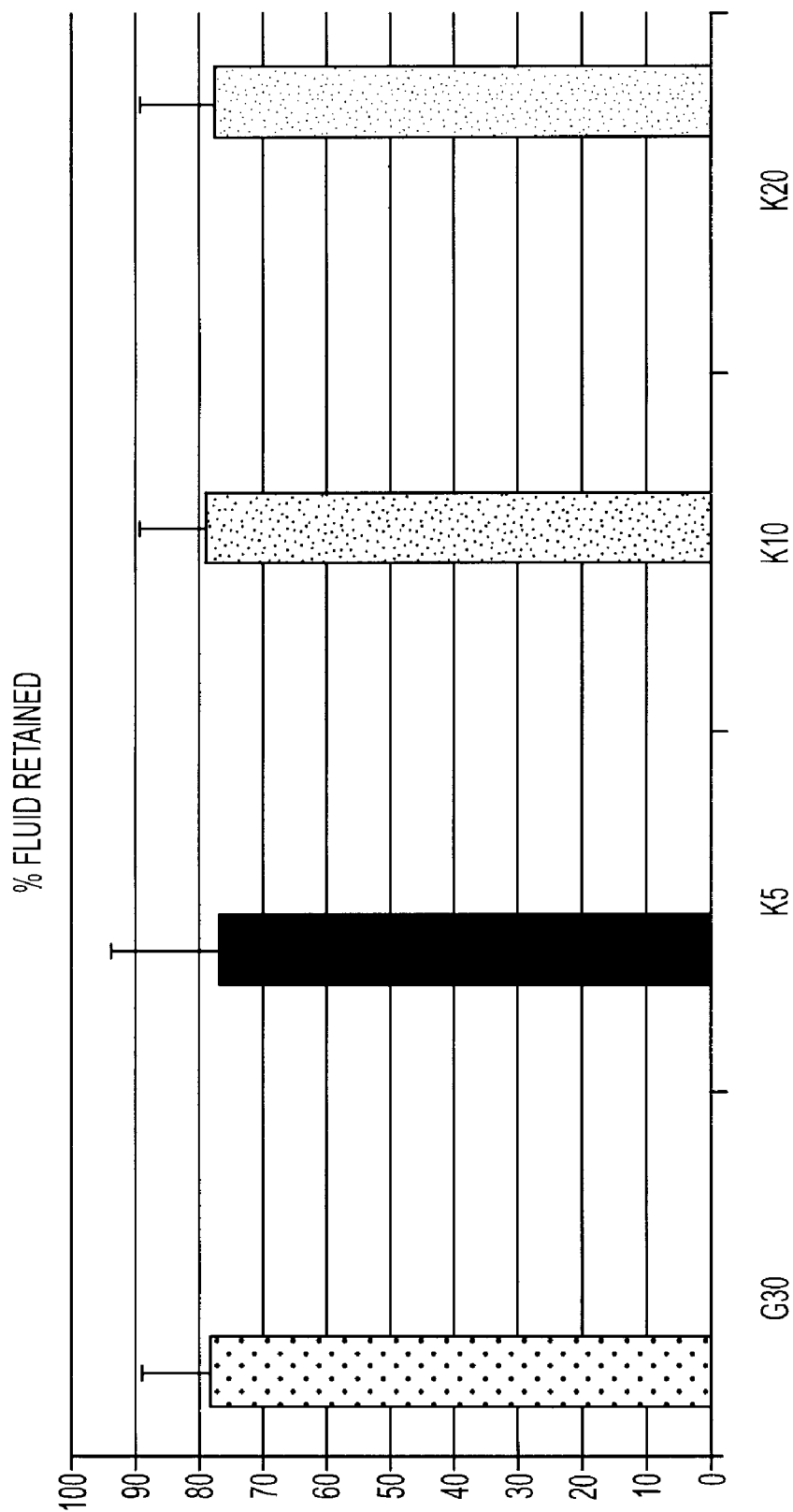
FIG. 31 shows the percent of total fluid retained at the end of the recovery period for various formulations.

Total cumulative fluid output was not different between treatments. Cumulative fluid output was 353.99±161.73 ml, 369.13±167.35 ml, 380.93±240.35 ml, and 386.93±205.07 ml, for G30, K5, K10, and K20, respectively. Urine output at each data collection point was also not different between treatments for any time point. The percent of fluid retained was not different between formulae (78.17±11.45% for G30, 76.60±16.84% for K5, 78.28±10.83% for K10, and 76.62±12.87% for K2). See FIG. 31. Relative to body weight, fluid retention did not differ either: 16.59±5.09 ml/kg, 17.29±5.04 ml/kg, 16.69±6.06 ml/kg, and 16.66±5.31 ml/kg for G30, K5, K10 and K20, respectively.

Figure 33:
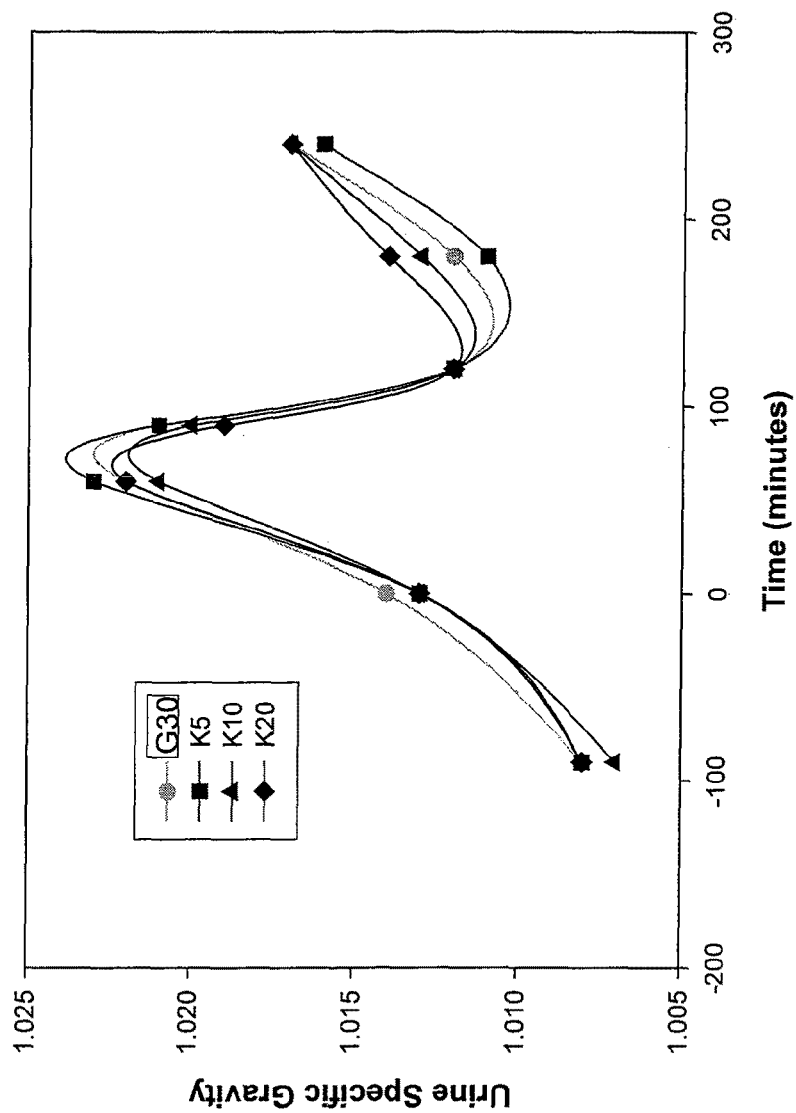
FIG. 33 shows the urine specific gravity over time—before and after exercise and during recovery—for various formulations.

Mean urine osmolality was also not different between treatments (G30=488±228 mOsm, K5=484±250 mOsm, K10=456±215 mOsm, K20=492±215 mOsm) nor was urine osmolality different at any time during recovery. See FIG. 32. Subjects began each exercise session well hydrated (USG=1.008±0.005). Urine specific gravity (USG) did not differ between treatments prior to exercise or at any time point during recovery. Similarly, the change in urine specific gravity did not different between treatments See FIG. 33.

Average urine sodium concentration was not different across trials (54.73±34.53 mEq/L, 60.34±38.44 mEq/L, 53.31±32.56 mEq/L, 60.99±35.99 mEq/L for G30, K5, K10, and K20, respectively). Total sodium excretion (urine volume×urine sodium concentration) was also not different across trials (G30=20.61±10.12 mEq; K5=24.66±12.86 mEq; K10=21.65±10.28 mEq; K20=24.97±12.49 mEq).

Figure 34:
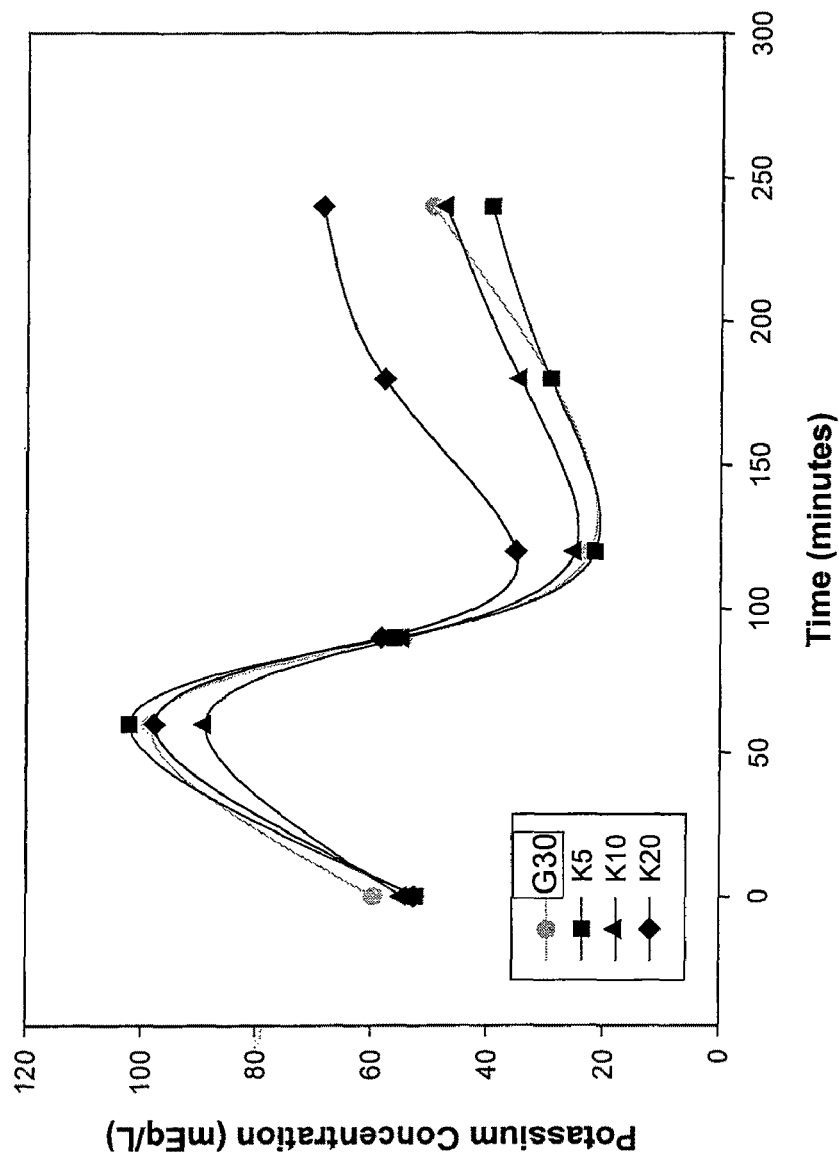
FIG. 34 shows the urine potassium concentration during the recovery period for various formulations.

The average urine potassium concentration was significantly higher for the K20 trial (56.59±33.43 mEq/L) compared to G30 (49.79±32.87 mEq/L), K5 (47.24±36.11) and K10 (46.87±28.96). The latter three were not different from each other. See FIG. 34

Figure 35:
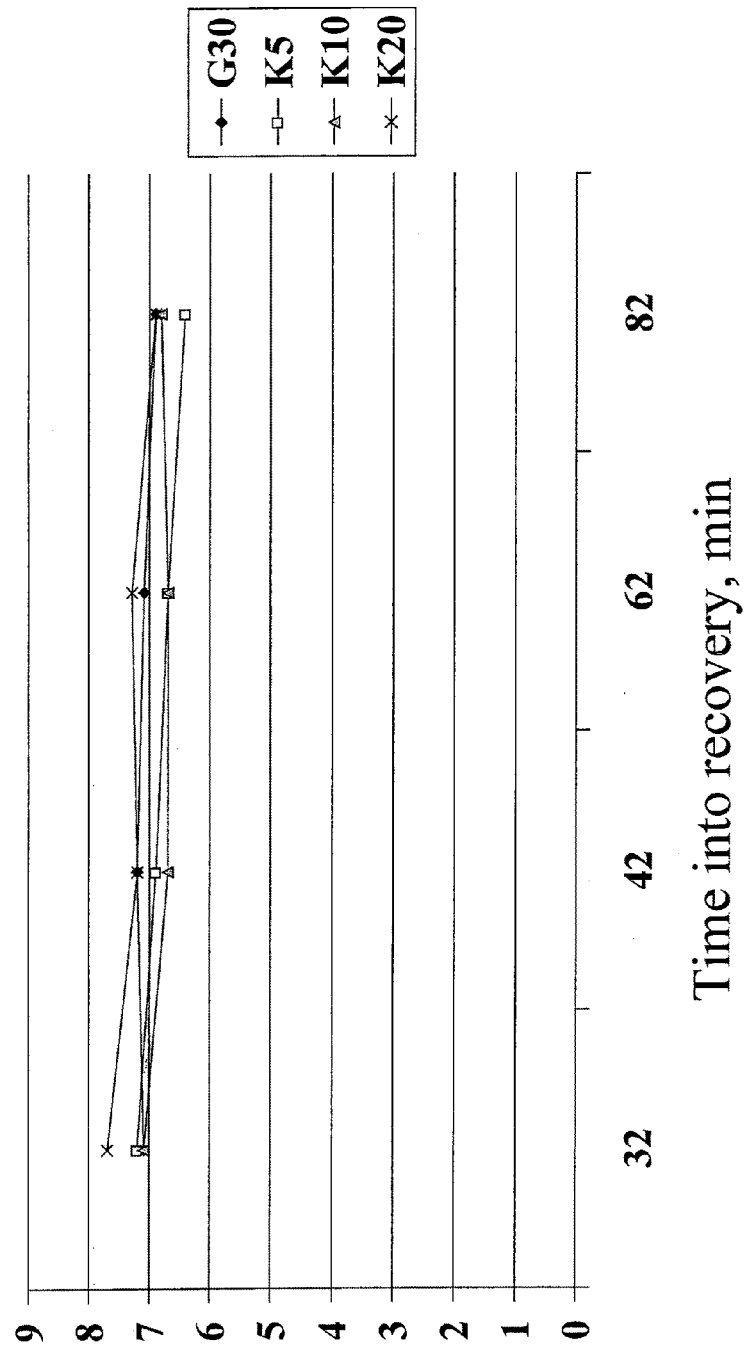
FIG. 35 shows the overall acceptance ratings from the sensory evaluations for various formulations.

Overall acceptance as determined from the sensory ratings during the rehydration period showed no differences between the beverages. See FIG. 35.

Although this invention has been described in terms of certain preferred compositions and certain discrete methods, other embodiments that may be apparent to those skilled in the art are also within the scope of this invention. Accordingly, the scope of the invention is intended to be determined by reference to the appended claims.

The invention claimed is:

1. A beverage composition, consisting essentially of:
    a) about 4 to about 10% by weight of a carbohydrate source;
    b) from about 30 to about 40 mEq/L of sodium;
    c) from about 11 to about 18 mEq/L of chloride;
    d) at least about 3 to about 20 mEq/L of potassium; and
    e) optionally, comprising at least one compound selected from the group consisting of a flavoring, a clouding agent, and citric acid,
    f) water,
    wherein said beverage composition has an osmolality of about 250 to about 350 mOsm/Kg, and said beverage composition contains an amount of sodium and chloride to cause at least about 80% fluid retention in a human subject after exercise, and does not have a negative sensory attribute.

2. The beverage composition of claim 1 wherein said sodium comprises from about 33 to about 40 mEq/L.

3. The beverage composition of claim 1, wherein said carbohydrate source is about 4.5 to about 6.5% by weight.

4. The beverage composition of claim 1, wherein said carbohydrate source is a mixture of at least three components, including fructose and two components selected from the group consisting of sucrose, maltose, maltodextrin, glucose, galactose, trehalose, fructo-oligosaccharides, beta-glucan, and trioses.

5. The beverage composition of claim 4, wherein said carbohydrate source is a mixture of sucrose, glucose, and fructose.

6. The beverage composition of claim 5, wherein said sucrose is about 1 to about 5% by weight.

7. The beverage composition of claim 5, wherein said glucose is about 1 to about 2.5% by weight.

8. The beverage composition of claim 5, wherein said fructose is about 0.8 to about 1.8% by weight.

9. The beverage composition of claim 5, wherein said sucrose, glucose, and fructose are about 3%, about 1.7%, and about 1.3%, respectively, by weight.

10. The beverage composition of claim 1, wherein said potassium is about 3 to about 16 mEq/L.

11. The beverage composition of claim 1, wherein said beverage composition comprises at least one compound selected from the group consisting of a flavoring agent, a clouding agent, and citric acid.

12. The beverage composition of claim 11, wherein said flavoring agent is less than about 0.4% by weight of the composition.

13. The beverage composition of claim 11, wherein said clouding agent is less than about 100 parts per million.

14. The beverage composition of claim 11, wherein said citric acid is about 0.24% to about 0.45% by weight.

15. The beverage composition of claim 1, wherein said beverage composition is a concentrate.

16. A beverage composition, consisting essentially of:
a) a mixture of about 3% by weight of sucrose, about 1.7% by weight of glucose, and about 1.3% by weight of fructose; wherein the fructose amount is less than that of the sucrose amount;
b) about 30 mEq/L of sodium;
c) from about 11 to about 18 mEq/L of chloride;
d) from about 3 to about 20 mEq/L of potassium; and
e) water,
wherein said beverage composition has an osmolality of about 250 to about 350 mOsm/Kg, and said beverage composition contains an amount of sodium and chloride to cause at least about 80% fluid retention in a human subject after exercise, and does not have a negative sensory attribute.

* * * * *